US012761092B2

(12) United States Patent
Van Den Dungen et al.

(10) Patent No.: US 12,761,092 B2
(45) Date of Patent: Oct. 13, 2026

(54) DEVICE, SYSTEM AND MANUFACTURING METHOD FOR ELECTRONIC STRAIN SENSOR

(71) Applicants: SLEEPTITE PTY LTD, Hawthorn (AU); ROYAL MELBOURNE INSTITUTE OF TECHNOLOGY (RMIT UNIVERSITY), Melbourne (AU); SLEEPEEZEE BEDDING AUSTRALIA PTY LTD (SLEEPEEZEE), Campbellfield (AU)

(72) Inventors: Cameron Van Den Dungen, Braeside (AU); Sharath Sriram, Melbourne (AU); Madhu Bhaskaran, Melbourne (AU); Sumeet Walia, Melbourne (AU); Bill Mantzis, Campbellfield (AU); Dashen Dong, Melbourne (AU); Harry Lee, Campbellfield (AU)

(73) Assignees: SLEEPTITE PTY LTD, Hawthorn (AU); ROYAL MELBOURNE INSTITUTE OF TECHNOLOGY (RMIT UNIVERSITY), Melbourne (AU); SLEEPEEZEE BEDDING AUSTRALIA PTY LTD (SLEEPEEZEE), Campbellfield (AU)

( * ) Notice: Subject to any disclaimer, the term of this patent is extended or adjusted under 35 U.S.C. 154(b) by 608 days.

(21) Appl. No.: 18/034,573

(22) PCT Filed: Oct. 28, 2021

(86) PCT No.: PCT/AU2021/051257

§ 371 (c)(1),
(2) Date: Apr. 28, 2023

(87) PCT Pub. No.: WO2022/087670

PCT Pub. Date: May 5, 2022

(65) Prior Publication Data

US 2023/0400369 A1 Dec. 14, 2023

(30) Foreign Application Priority Data

Oct. 29, 2020 (AU) ................................ 2020903914

(51) Int. Cl.
*G01L 1/22* (2006.01)
*H05K 1/03* (2006.01)
(Continued)

(52) U.S. Cl.
CPC .......... *G01L 1/2287* (2013.01); *H05K 1/0353* (2013.01); *H05K 1/038* (2013.01);
(Continued)

(58) Field of Classification Search
CPC .... H05K 1/0353; H05K 1/038; H05K 1/0386; H05K 1/092; H05K 1/189; H05K 3/284;
(Continued)

(56) References Cited

U.S. PATENT DOCUMENTS 9,851,267 B1 * 12/2017 Ma ............................ G01L 1/20
2010/0130889 A1 5/2010 Toth et al.
(Continued)

FOREIGN PATENT DOCUMENTS

CN 110068404 7/2019
CN 110333010 10/2019
(Continued)

OTHER PUBLICATIONS

International Search Report PCT/AU2021/051257 dated Dec. 24, 2021—9 pages.
Written Opinion PCT/AU2021/051257 dated Dec. 24, 2021—16 pages.

*Primary Examiner* — Kyung S Lee
(74) *Attorney, Agent, or Firm* — K&L Gates LLP

(57) ABSTRACT

The present disclosure generally relates to an electronic strain sensor, a system incorporating the sensor, and a
(Continued)

method of manufacturing the sensor. The present disclosure also relates to methods of measuring one or more physiological parameters of a living subject, or methods of diagnosing a sleep-related disorder of a living subject, the methods comprising sensing a signal produced by the living subject with the electronic strain sensor or system. The strain sensor comprises: an electrode layer printed on a substrate, a sensing layer printed on a portion of the electrode layer, and an encapsulation layer encapsulating the electrode and sensing layers. The electrode layer exhibits a sheet resistance less than that of the sensing layer, and the sensing layer is in direct contact with the electrode layer. The sensor's electrical resistance can be increased through forming microscopic cracks in the sensing layer in response to forces applied to the sensor.

25 Claims, 14 Drawing Sheets

(51) Int. Cl.

| | |
|---|---|
| ***H05K 1/09*** | (2006.01) |
| ***H05K 1/189*** | (2026.01) |
| ***H05K 3/28*** | (2006.01) |
| *A61B 5/00* | (2006.01) |
| *A61B 5/11* | (2006.01) |

(52) U.S. Cl.
CPC ........... *H05K 1/0386* (2013.01); *H05K 1/092* (2013.01); *H05K 1/189* (2013.01); *H05K 3/284* (2013.01); *A61B 5/1126* (2013.01); *A61B 5/4806* (2013.01); *H05K 2201/05* (2013.01); *H05K 2201/10151* (2013.01); *H05K 2203/1305* (2013.01)

(58) Field of Classification Search
CPC ....... G01L 1/2287; G01L 1/20; A61B 5/4806; A61B 5/6892; A61B 2562/0261; A61B 2562/12
See application file for complete search history.

(56) References Cited

U.S. PATENT DOCUMENTS

| | | | |
|---|---|---|---|
| 2013/0133435 | A1 | 5/2013 | Muramatsu et al. |
| 2016/0340534 | A1* | 11/2016 | Wijesundara .......... C09D 11/52 |
| 2017/0241847 | A1* | 8/2017 | Loh ........................... G01L 1/18 |
| 2017/0303853 | A1* | 10/2017 | McMillen ............ A61B 5/6843 |
| 2018/0160979 | A1 | 6/2018 | Kim et al. |
| 2019/0142097 | A1 | 5/2019 | Moor |
| 2020/0150761 | A1* | 5/2020 | Hogbin .................... G01B 7/30 |
| 2020/0375537 | A1 | 12/2020 | Carlile et al. |
| 2022/0117503 | A1* | 4/2022 | Wang ................. A61B 5/14521 |

FOREIGN PATENT DOCUMENTS

| | | |
|---|---|---|
| WO | 2015040583 | 3/2015 |
| WO | 2019136143 | 7/2019 |
| WO | 2020243121 | 12/2020 |

* cited by examiner

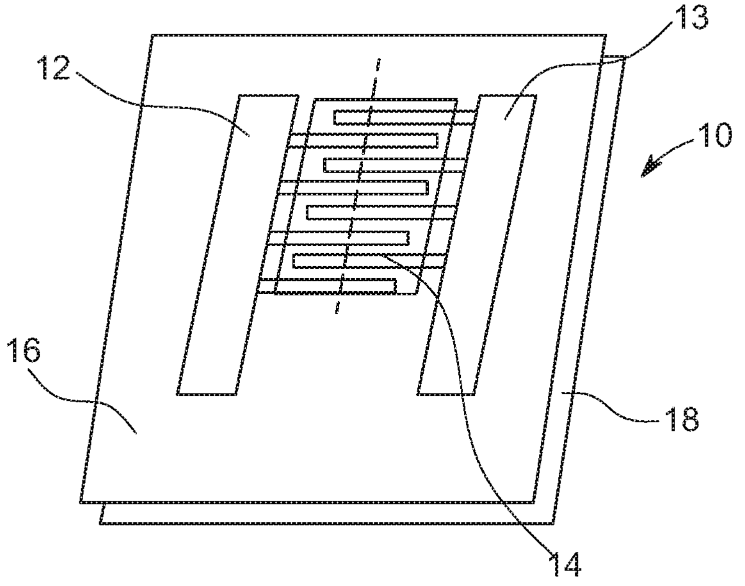
FIG. 2A(i)
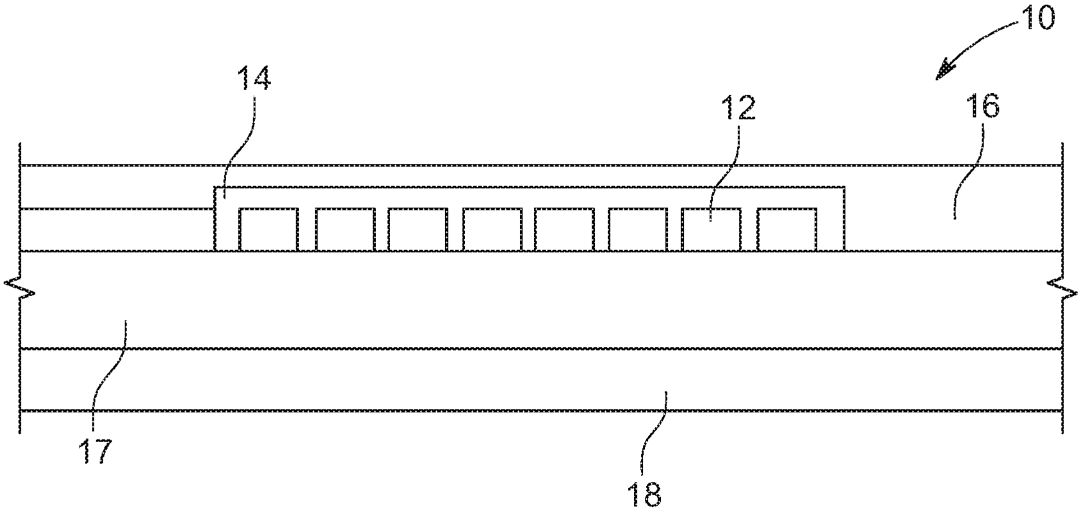
FIG. 2A(ii)

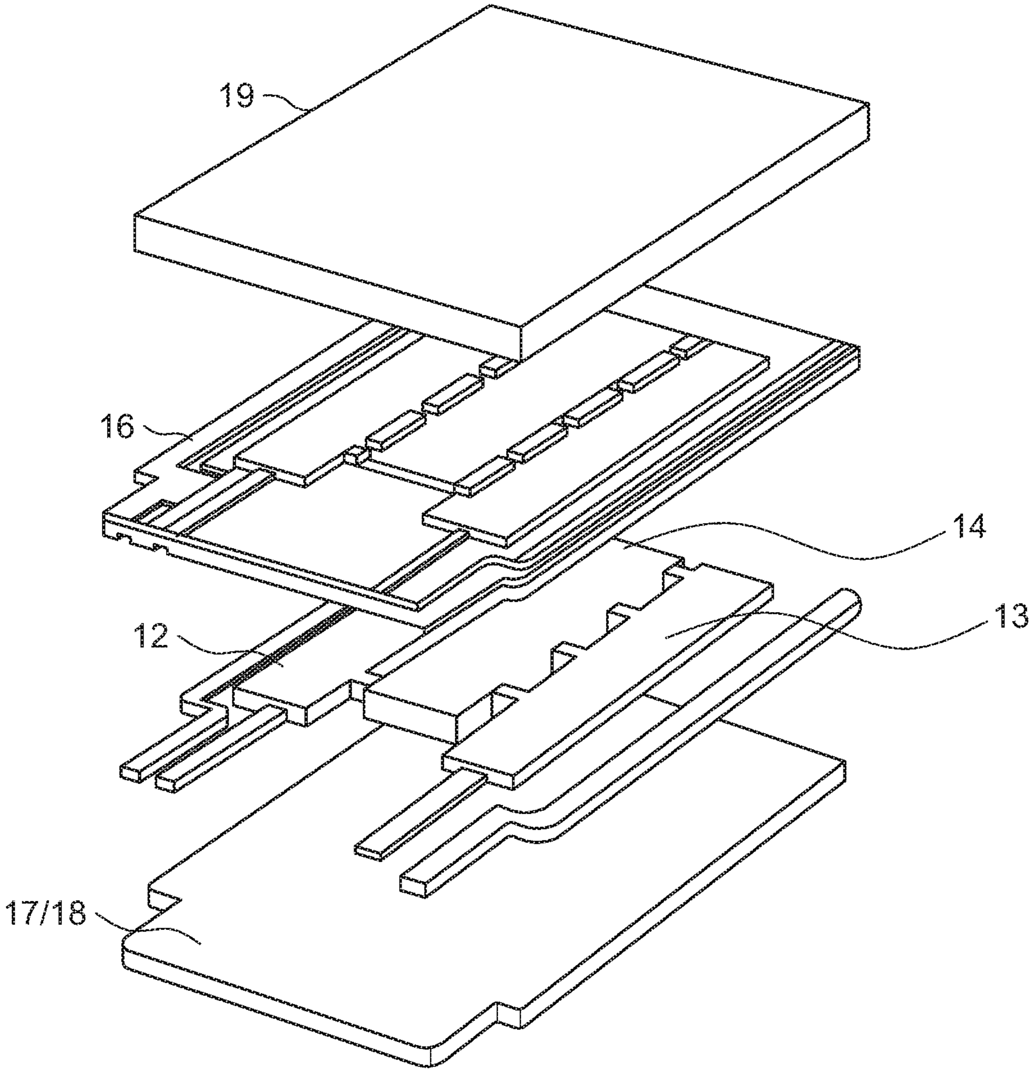
FIG. 2A(iii)

FIG. 4(a)(iii)

No strain

30% strain (a)

(b)

(e)

(a)

(b)

DEVICE, SYSTEM AND MANUFACTURING METHOD FOR ELECTRONIC STRAIN SENSOR

CROSS REFERENCE TO THE RELATED APPLICATIONS

This application is a national phase entry of PCT/AU2021/051257, filed Oct. 28, 2021, which claims priority to Australian Patent Application No. AU2020903914, filed Oct. 29, 2020, the entire disclosure of which are incorporated by reference herein.

TECHNICAL FIELD

The present disclosure generally relates to an electronic strain sensor, a system incorporating the sensor, and a method of manufacturing the sensor. The present disclosure also relates to methods of measuring one or more physiological parameters of a living subject, or methods of diagnosing a sleep-related disorder of a living subject, the methods comprising sensing a signal produced by the living subject with the electronic strain sensor or system.

BACKGROUND

Sleep is a natural function of the human body and accounts, on average, for one third of human lifetime. Sleep is important in addressing mental and physical fatigue accumulated during the day, and strengthens our immune function which can deeply affect quality of life. Therefore, constant monitoring of body movement, breathing, and heartbeat during different sleeping stages has attracted great interest in terms of early-stage disease diagnosis, as well as the detection of sleep disorders. Further, analysis of data collected from monitoring systems, and delivery of results to clinicians or paramedics, can help improve the diagnosis, monitoring, and clinical outcomes in patients exhibiting heart, lung and sleep disorder symptoms, thereby improving overall life quality.

Technological evolution, particularly in the past few decades, has accelerated the development of different products for monitoring the quality of sleep. For example, ear-electroencephalography (EEG) and ear-electrocardiograph (ECG) sensors have been used for sleep staging and heart rate recording. Body mounted strain gauge sensors have been used for monitoring physical movements, respiration and heartbeat. These types of sensors are worn, and can therefore cause discomfort, and ultimately affect the quality of sleep. Non-wearable monitoring systems can address this issue and provide minimal interference. For example, radar and/or depth cameras can be used to measure chest and abdominal movements. Additionally, near-infrared (IR) camera imagery can be used to project and track IR dots to analyse the respiration rate. Aside from privacy concerns, the cost and energy consumption of camera based systems make them impractical for every-day consumer use. An alternative is piezoelectric based sensor systems. Such systems typically use very low power, and can comprise ceramic sensors placed under a mattress to obtain pressure data (including heartrate, breath rate, sleep cycles and movements). There are some commercial non-wearable products for sleep monitoring in hospital and home based on piezoelectric sensors. Nevertheless, apart from the very high purchase cost, such systems lack particular functions and/or sensitivity. For example, piezoelectric sensors are unable to recognise the direction of movement during the sleeping.

Therefore, there is a pressing need for a low cost, reliable, non-invasive sleep monitoring device and system. A non-wearable user experience that can minimise the interference on a user's sleep-state may provide more accurate data to clinicians as well as paramedics. In addition, the device and system needs to be adaptable for large scale manufacturing. Scalable, but low-cost production may rapidly advance uptake of the device and system by consumers, professionals and in clinical practice, therefore benefiting the health and wellbeing of the whole community.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject The present disclosure provides a non-invasive strain sensor, a non-invasive monitoring system, and a manufacturing method of the same. The present disclosure also provides methods of measuring at least one physiological parameter of a living subject, or methods of diagnosing a sleep-related disorder of a living subject, said methods comprising sensing a signal produced by the living subject with a strain sensor or system of the present disclosure.

According to one non-limiting aspect of the present disclosure, there is provided a method of manufacturing a strain sensor. In one embodiment, the method includes printing an electrode layer on a substrate with a first conductive ink; printing a sensing layer on the electrode layer; and encapsulating the electrode and sensing layers by applying a hot-melt layer. Preferably, the electrode layer and sensing layer are in direct contact.

In embodiments, the method further comprises applying heat to the hot-melt layer to adhere the sensor to a fabric, optionally wherein the sensor is integrated between two layers of fabric.

In embodiments, the electrode layer is generally elongate, the first and second electrode each comprise a head portion and tail portion, and the tail portions of the first and second electrode are substantially parallel. Preferably, the tail portions each comprise repeating wave patterns.

According to another non-limiting aspect of the present disclosure, there is provided a strain sensor. In embodiments, the strain sensor comprises an electrode layer provided printed on the a substrate, the electrode layer comprising a first conductive ink, a sensing layer provided printed on a portion of the electrode layer, the sensing layer comprising a second conductive ink, and an encapsulation layer which encapsulates the electrode layer and the sensing layer, wherein the sensing layer is in direct contact with the electrode layer.

In embodiments, the application of external force to or near the sensor generates microscopic cracks within the sensing layer increasing resistance, and the removal of the external force substantially eliminates the microscopic cracks within the sensing layer decreasing resistance.

According to another non-limiting aspect of the present disclosure, there is provided a monitoring system. In embodiments, the monitoring system comprises the above-mentioned sensor, and optionally communication unit configured to communicate sensed signals (i.e. changes in electrical resistance) to an external device. Communication between the communication unit and external device is preferably by wireless communication.

According to the present disclosure, a preferred outcome is that the monitoring device, system and manufacturing method can provide a low cost, reliable, and non-invasive way to monitor sleeping behaviour of a living subject. In this regard, according to another non-limiting aspect of the present disclosure, there is provided a method of measuring at least one physiological parameter produced by a living subject, the method comprising:

providing at least one flexible and stretchable strain sensor that comprises a substrate, an electrode layer provided on the substrate, a sensing layer provided on the electrode layer, and an encapsulation layer which encapsulates the sensing and electrode layers, contacting the subject with the strain sensor, wherein changes in the at least one physiological parameter results in changes to the electrical resistance of the at least one sensor, optionally receiving and transmitting the electrical resistance changes to an external device for reporting or analysis.

According to yet another non-limiting aspect of the present disclosure, there is provided a method of diagnosing a sleep-related disorder in a living subject, the method comprising:

receiving a signal comprising electrical resistance changes generated by at least one flexible and stretchable strain sensor that is in contact with the subject, wherein the sensor comprises a substrate, an electrode layer provided on the substrate, a sensing layer provided on the electrode layer, and an encapsulation layer encapsulating the electrode and sensing layers, and wherein the sensing layer is in direct contact with the electrode layer, optionally analysing the received signal to diagnose said disorder.

It should be understood that the outcomes described herein are not limited, and may be any of or different from the outcomes described in the present disclosure. To this point, other embodiments will be evident from the following detailed description of various aspects of the disclosure.

BRIEF DESCRIPTION OF THE FIGURES

Features of device, system and manufacturing method for a non-invasive strain sensor as described herein may be better understood by reference to the accompanying drawings in which:

FIG. 2A illustrates a schematic drawing of an electronic strain sensor according to an embodiment of the present disclosure; FIG. 2A(i) being a front perspective view of the sensor and FIG. 2A(ii) being a cross-section view according to the dashed line of FIG. 2A(i). FIG. 2A(iii) Illustrates an exploded view of an embodiment of the sensor.

FIG. 2B(i) shows a polyurethane substrate with two different shaped electrode layers, and FIG. 2B(ii) shows the electrode layers of FIG. 2B(i) with a sensing layer and an encapsulation layer.

FIG. 2D(ii) illustrates another embodiment of an arrangement of an electronic strain sensor of the present disclosure in a mattress cover. The figure is an exploded view of multiple sensors arranged in an array.

FIG. 3 (*b*) illustrates a screen mask design of rectangular pattern for a sensor layer according to an embodiment of the present disclosure.

FIGS. 4 (*b*) and (*c*) are photos of twisting and stretching the printed electrodes to demonstrate the flexibility and stretchability.

FIG. 5 (*b*) illustrates a resistance curve of a hand press test on top of a mattress cover with an embedded strain sensor according to an embodiment of the present disclosure; FIG. 5 (*c*) illustrates a resistance curve of body movement obtained when a user is lying on top of a mattress cover with an embedded strain sensor; and FIG. 5 (*d*) illustrates a resistance curve of a user generated over 90 mins where the user is breathing deeply and laying on top of a mattress cover with an embedded strain sensor according to an embodiment of the present disclosure; and FIG. 5 (*e*) is an enlargement of the resistance curve shown in (d) for the period between 18 and 36 mins.

FIG. 6 (*b*) illustrates a hand press test resistance curve generated by an embedded strain sensor in a mattress cover that has previously undergone 10,000 rollator cycles.

DETAILED DESCRIPTION

Figure 1:
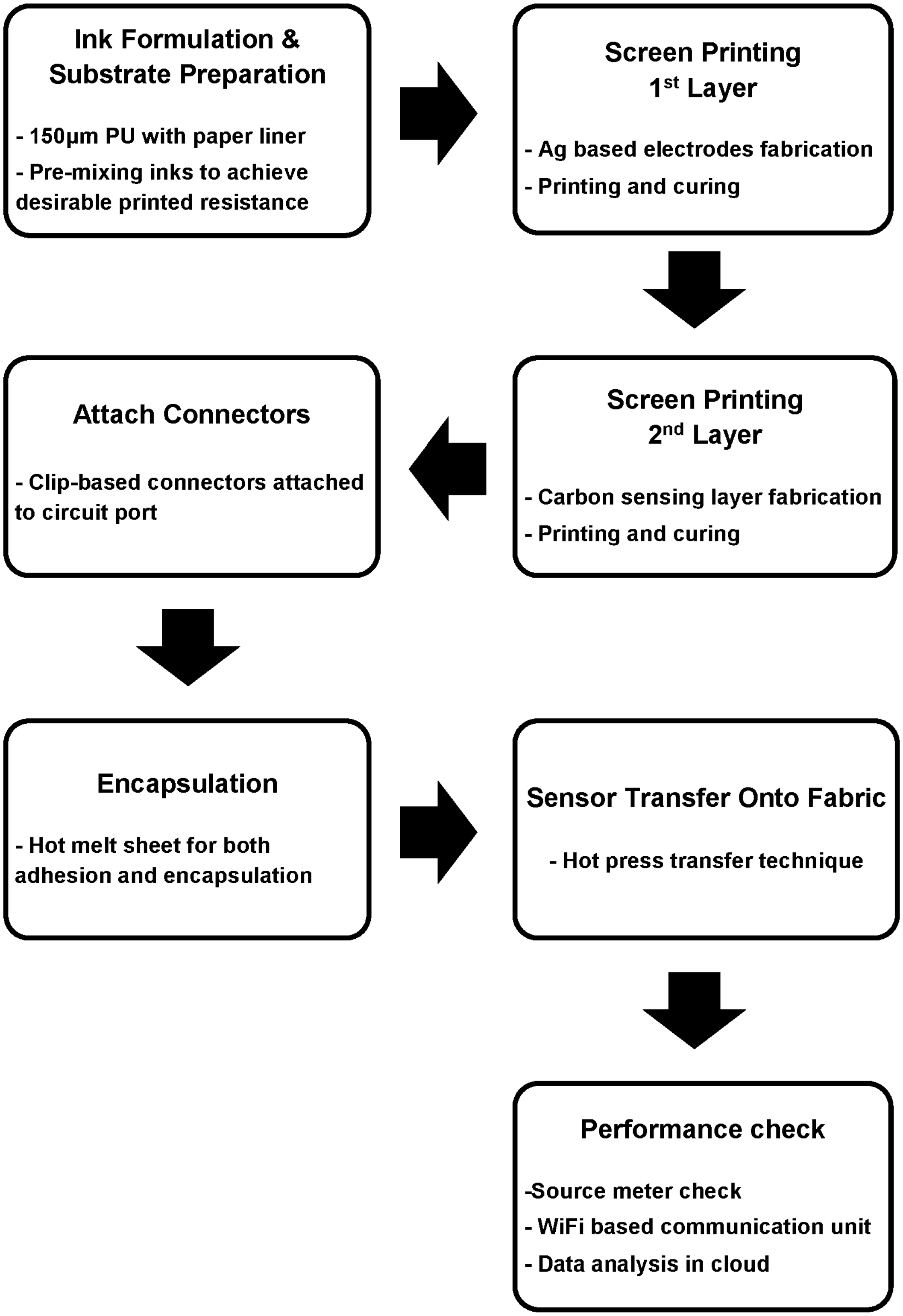
FIG. 1 illustrates a workflow for manufacturing an electronic strain sensor on fabric according to an embodiment of the present disclosure.

Aspects and embodiments will now be described more fully hereinafter with reference to the accompanying drawings, in which some, but not all embodiments of the present disclosure are shown. Indeed, the technology of the present disclosure may be embodied in many different forms and should not be construed as limited to the embodiments set forth herein.

Likewise, many modifications and other embodiments of the device, system and method described herein will come to mind to one of skill in the art to which the disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

Throughout the specification and claims, terms may have nuanced meanings suggested or implied in context beyond an explicitly stated meaning. Likewise, the phrase "in an embodiment" as used herein does not necessarily refer to the same embodiment or implementation and the phrase "in another embodiment" as used herein does not necessarily refer to a different embodiment or implementation. It is intended, for example, that claimed subject matter includes combinations of exemplary embodiments or implementations in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" or "at least one" as used herein, depending at least in part upon context, may be used to describe any feature, structure, or characteristic in a singular sense or may be used to describe combinations of features, structures or characteristics in a plural sense. Similarly, terms, such as "a", "an", or "the", again, may be understood to convey a singular usage or to convey a plural usage, depending at least in part upon context. In addition, the term "based on" or "determined by" may be understood as not necessarily intended to convey an exclusive set of factors and may, instead, allow for existence of additional factors not necessarily expressly described, again, depending at least in part on context.

Unless defined otherwise, all technical and scientific terms used herein have the same meaning as commonly understood by one of skill in the art to which the disclosure pertains. Although any methods and materials similar to or equivalent to those described herein may be used in the practice or testing of the present disclosure, the preferred methods and materials are described herein.

The method steps, processes, and operations described herein are not to be construed as necessarily requiring their performance in the particular order discussed or illustrated, unless specifically identified as an order of performance. It is also to be understood that additional or alternative steps may be employed.

Except where otherwise indicated, all numbers expressing quantities, or reaction conditions, and so forth used in the specification and claims are to be understood as being modified in all instances by the term "about". Accordingly, unless indicated to the contrary, the numerical parameters set forth in the specification and claims are approximations that may vary depending upon the desired properties sought to be obtained by the present disclosure. At the very least, each numerical parameter should be construed in light of the number of significant digits and ordinary rounding conventions. The term "about" may be understood to refer to a range of +/−10%, such as +/−5% or +/−1% or, +/−0.1%.

Recitation of ranges of values herein is merely intended to serve as a shorthand method of referring individually to each separate value falling within the range. Unless otherwise indicated herein, each individual value is incorporated into the specification as if it were individually recited herein. For example, if a range is from about 1 to about 50, it is deemed to include, for example, 1, 7, 34, 46.1, 23.7, or any other value or range within the range.

The terminology used herein is for the purpose of describing particular example embodiments only and is not intended to be limiting. The terms "comprise", "comprises", "comprised" or "comprising", "including" or "having" and the like in the present specification and claims are used in an inclusive sense, that is to specify the presence of the stated features but not preclude the presence of additional or further features.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments so claimed are inherently or expressly described and enabled herein.

As used herein, "diagnosis" or "diagnosing" refers broadly to classifying a disease or condition, or a symptom thereof, determining a severity of the disease/condition/symptom, monitoring disease/condition/symptom progression, forecasting an outcome of a disease/condition/symptom and/or prospects of recovery. The terms "detecting" or "predicting" may also optionally encompass any of the foregoing.

The present disclosure generally relates to a non-invasive monitoring device, a non-invasive monitoring system, and a manufacturing method of the same. More specifically, the present disclosure provides for the use of a non-invasive monitoring device, or a non-invasive monitoring system, in the detection of one or more physiological parameters of a living subject including body movement, pressure change and respiration. In embodiments, the one or more physiological parameters are measured when the subject is horizontally positioned on a mattress, in a non-invasive manner and without the sensor directly contacting the subject's skin. The present disclosure provides methods of measuring sleep behaviour, and/or diagnosing sleep-related disorders including insomnia, snoring, sleep apnoea, parasomnia and restless leg syndrome. Measuring sleep and/or diagnosing sleep-disorders can be useful in identifying or predicting other health problems such as high blood pressure, heart disease, diabetes, and stroke. Decreased sleep duration and/or quality, may cause problems in concentration and attention, as well as poor judgment, during the day. In the elderly, a common cause of injury is falls, where it is recognised that poorer sleep quality during the night is a risk factor. The present disclosure may also beneficially provide a method of manufacturing a non-invasive sleep monitoring device and non-invasive sleep monitoring system in large scale with low cost.

In one aspect of the present disclosure, there is provided a non-invasive strain sensor. In embodiments, the non-invasive strain sensor comprises flexible and stretchable electronics, and can be embedded in a mattress cover, for example, to constantly monitor one or more physiological parameters of a living subject during sleep. Unlike conventional rigid bed sensors that are normally placed underneath a mattress, the non-invasive strain sensor of the present disclosure can be directly embedded in to a mattress cover through a proprietary manufacturing process. This provides a number of advantages, including excellent sensor sensitivity, flexibility, stretchability and durability. In embodiments, strain sensors of the present disclosure may be employed to work on any type of mattress rather than one specific type of mattress. Further, strain sensors of the present disclosure may be used to detect one or more physiological parameters of a living subject, including body movement, pressure or weight change and breathing. In embodiments, strain sensor electrical resistance changes can be read in real-time and collected in an indirect manner in contrast to wearable sensors requiring direct body contact. In further embodiments, strain sensor electrical resistance changes may be stored in a computer readable storage medium (locally or remotely) for subsequent analysis.

In embodiments, the strain sensor of the present disclosure may be incorporated in any item designed to support the body weight of a living subject, or a portion thereof. For example, strain sensors of the present disclosure may be incorporated into covers for chairs (such as a recliner), cushions, or pillows.

In embodiments, the strain sensor (or an array strain sensors) of the present disclosure may be connected to a wireless communication device, whereby the collected signals (i.e. comprising changes in electrical resistance) may be uploaded into a cloud-based data platform as well as to a mobile device, such as a smartphone. A caregiver (i.e. clinicians, paramedics and/or family members) tasked with monitoring the living subject may then access these data anytime or anywhere, and be notified if any signals become abnormal. In addition, the strain sensor of the present disclosure may enable a caregiver to be alerted of unexpected movement or lack thereof. As such, the strain sensor may enable those monitoring a subject to determine or be alerted to how long a subject has been out of bed during night time, or to provide a reminder to check on a subject's condition.

In contrast to conventional monitoring systems that require either a direct skin contact monitoring product (such as a wearable) or an external monitoring device (such as IR camera), the flexible and stretchable strain sensors of the present disclosure provide an alternative, non-wearable user experience that is comfortable while providing accurate physiological measurements. In addition, where a strain sensor of the present disclosure is embedded into a mattress cover, the cover may be manufactured to suit a wide range of mattress materials and sizes, reducing the cost when compared to other smart-bed products that may require integration into a mattress during manufacture. On the other hand, the low-cost advantage is not only reflected in the possibility to adapt the strain sensor for use with pre-existing products, but also in the strain sensor manufacturing process itself.

According to another non-limiting aspect of the present disclosure, there is provided a method of manufacturing a flexible and stretchable strain sensor. FIG. 1 illustrates the overall working flow of an embodiment of said manufacturing method. First, a thermoplastic polyurethane (PU) ester grade film comprising a paper liner is used as a substrate for the flexible sensor. The substrate has a preferable thickness of about 150 μm. The substrate may have an alternative thickness ranging from about 50-about 1000 μm depending on other variables in the manufacturing process.

Pre-mixed inks for achieving desirable strain sensor electrode resistance are preferred. More specifically, in embodiments, the strain sensor and method of manufacturing said sensor of the present disclosure rely on conductive inks. Further preferably, the conductive inks are printable inks. In general, a suitable conductive ink includes a carrier (e.g. a liquid solvent that evaporates after deposition) and particles of one or more conductive material, or other functional material that remain on the substrate to which the ink is applied. Any type of conductive material can be utilised so long as a particle size of the conductive material is suitable for process being used to apply the conductive material to the substrate. For example, the conductive material can be selected from a group consisting of aluminium, gold, silver, copper, carbon, graphene, and platinum, or combinations thereof. The conductive ink can be cured using any suitable curing process.

In embodiments, a conductive ink suitable for printing the sensor of the present disclosure is a silver (Ag) ink that contains conductive components including Ag particles, epoxy, ethyl acetate, isopropanol and isopropyl acetone. In embodiments, the silver ink may include polyester resin with about 10-20 weight %, conductive silver powder with about 65-85 weight %, solvent with about 10-15 weight % and filler with about 1-5 weight %. In embodiments, carbon (C) ink is another preferred ink and may contain conductive components including carbon black and/or graphite, epoxy, ethyl acetate, isopropanol and isopropyl acetone. In yet another embodiment, a preferably carbon ink may include polyvinylidene chloride with about 10-20 weight %, carbon black with weight % from about 1%-5%, dibasic ester solvent with about 60-70 weight % and graphite with about 10-20 weight %. The desirable printed resistance is, but not limited to, from about 100 to about 10,000 ohm. Further preferably, inks suitable for printing the sensor of the present disclosure are inks that have elastomeric properties. That is, preferred inks are those which are flexible and stretchable.

As shown in FIG. 1, after ink formulation and substrate preparation, Ag-based electrodes are printed on the substrate. In embodiments, printing is by a screen printing method. The screen printing method may include a stainless steel mask, preferably a mask with about 60-130 threads/cm, further preferably a mask with about 65-120 threads/cm. A squeegee suitable for the screen printing method preferably has a hardness between about 60-90 durometer range. Application of ink by the squeegee is subsequently followed by drying preferably at ambient temperature. Other mask types, such as polyester screen with about 50-100 threads/cm could also be used. In embodiments, other types of printing technologies (2D or 3D) may be employed to print the conductive ink-containing sensors of the present disclosure.

FIG. 1 shows that a carbon-based sensing film is then provided on top of the Ag-based electrodes by a subsequent screen printing step. The carbon-based sensing film is created by screen printing with a carbon-containing ink, preferably an ink comprising polyvinylidene chloride with about 10-20 weight %, carbon black with weight % from about 1%-5%, dibasic ester solvent with about 60-70 weight % and graphite with about 10-20 weight %. As noted further below, the ink used to create the sensing film preferably has different properties to the ink used to print the electrodes. For example, the ink used to create the sensing layer may be configured to form cracks when the sensor is in use, whereas the ink used to create the electrode layer preferably does not form cracks. After printing and curing the carbon-based sensing film, clip-based connectors (for example, CJT, A2550-TP-CR, or 2.54 mm pitch FFC crimp flex connector) are attached to the circuit port.

FIG. 1 additionally shows that a hot melt adhesive layer, preferably solvent-free ether or ester based (for example, DINGZING® Advanced Materials Inc., cat no. FS3258) for both adhesion and encapsulation is then applied to the sensor, thus completing fabrication of the flexible and stretchable strain sensor. Examples of suitable hot-melt sheet properties are summarised in Table 2. The fabricated strain sensor can be transferred onto a surface, such as a fabric, by hot press transfer technology or other lamination or heating techniques (for example, adhesion using light or temperature curable polymers). Generally, the temperature for adhering the fabricated sensor to a surface is sufficient to melt the hot melt adhesive layer, but insufficient to melt the substrate layer.

A performance check of the flexible sensor is preferably performed by source meter, a Wi-Fi® based communication unit and/or other devices for measuring current. Signal data may be reviewed an interpreted in real-time. Alternatively, collected signal data may be stored locally or remotely for subsequent analysis. Further, data analysis of the collected signals from the flexible sensor can be performed by a computer, mobile device or cloud computing device, or combinations thereof.

FIG. 2A(i), is a schematic drawing of a strain sensor structure according to an embodiment of the present disclosure. FIG. 2A(ii) is an enlarged cross-section of the top portion of the strain sensor structure wherein the direction of the cross-section is reflected by the dashed line show in FIG. 2A(i) and detailing the left side of the sensor. According to FIG. 2A(i), the sensor (10) according to this embodiment preferably includes an interdigitated electrode layer comprising a first electrode (12) and a second electrode (13), a sensing layer (14), a hot-melt adhesive based encapsulation layer (16) a polyurethane (PU) substrate (17) with paper liner (18). Each electrode (12, 13) is generally elongate and comprises a head portion and a tail portion, where each head portion provides a plurality of digitations (i.e. finger-like protuberances). Preferably, each electrode (12, 13) comprises from 3 to 12 digitations, further preferably 5 to 8 digitations, most preferably 6 digitations. The interdigitated electrode layer (12, 13) may comprise at least one of Ag, gold (Au), copper (Cu) and carbon (C), or a combination thereof, preferably Ag. The thickness may range from about 100 nm to about 100 μm. As shown in FIG. 2A, the sensing layer may cover a portion of the electrodes (12, 13), preferably the head portion of the electrodes, further preferably the sensing layer is confined to interdigitated portion of the electrodes. The sensing layer (14) may have a rectangular shape, a round shape or any other suitable shapes. The sensing layer may include at least one of conductive carbon (C), conductive metal (e.g. Au, Ag, Cu, or combinations thereof), conductive polymer, and conductive metal/polymer composites, or combinations thereof. The thickness may range from about 100 nm to about 100 μm. The hot-melt adhesive based encapsulation layer (16) may include at least one PU sheet with hot melt characteristics and comprise an ester- or ether-based film. The adhesive based encapsulation layer (16) thickness may range from about 10 μm to about 100 μm. The PU substrate (17) may comprise at least one ester- or ether-based film and its thickness may range from about 50 to about 1000 μm. The melting point of the adhesive based encapsulation layer (16) is less than that of the PU substrate (17). In embodiments, the melting point of the adhesive based encapsulation layer (16) is between about 85° C. to about 145° C., preferably less than about 100° C. In embodiments, the PU substrate (17) may have a melting point between about 85° C. to about 175° C., preferably above about 100° C., further preferably about 150° C.

FIG. 2A(iii) provides an exploded perspective view of an embodiment of the flexible and stretchable strain sensor of the present disclosure. Shown are electrodes (12, 13), sensing layer (14), encapsulation layer (16) and substrate layer with paper liner (17, 18). In this particular embodiment, the hot melt encapsulation layer (16) is used to adhere the sensor to a fabric layer (19).

Figure 2B:
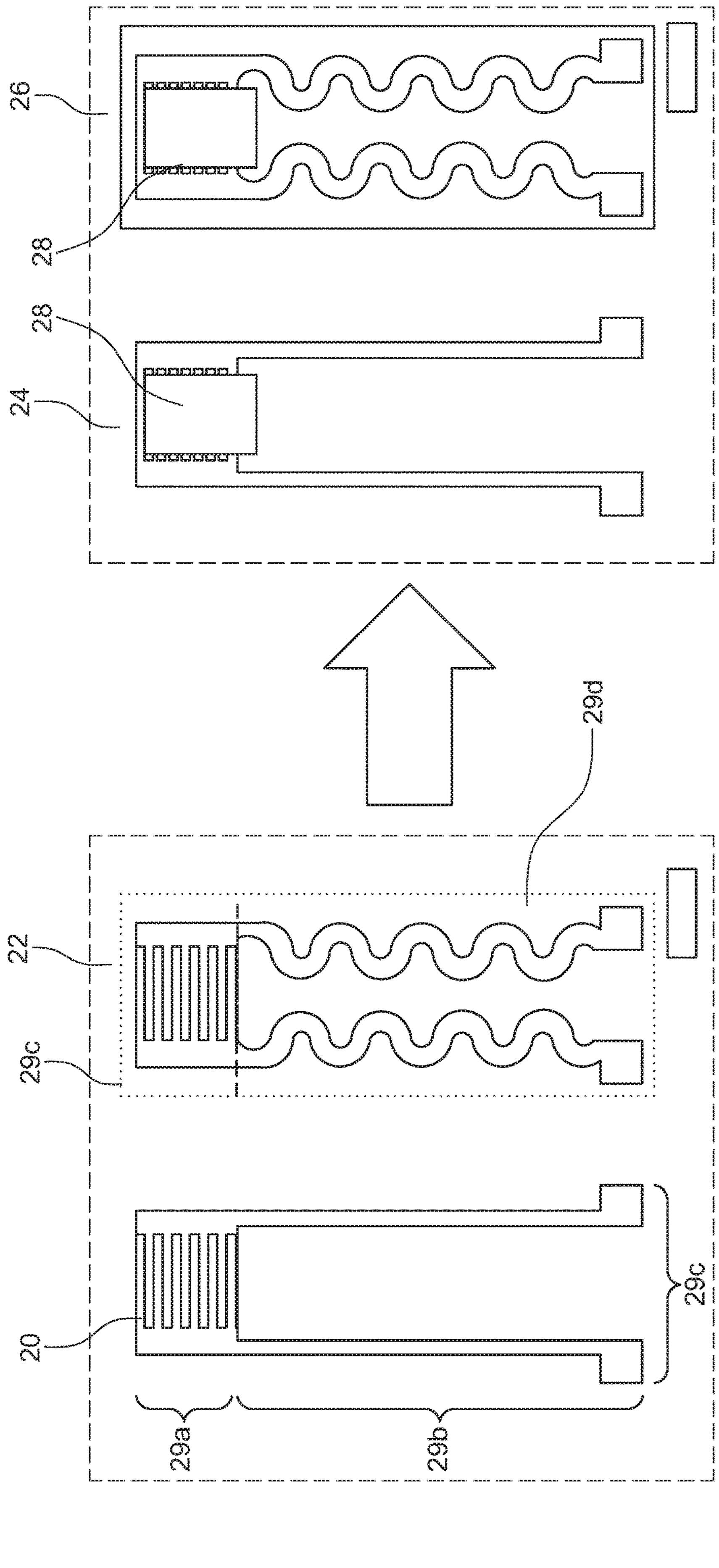
FIG. 2B provides photographs of the electronic strain sensor after different stages of a printing process (scale bar is 1 cm)

In FIG. 2B, embodiments of strain sensor electrode layer are shown with two types of electrode tails. According to FIG. 2B(i), photographs of two electrode layers on a substrate layer are shown. In one embodiment one electrode layer (20) comprises two interdigitating left and right electrodes each having tails which are substantially linear (straight), and in another embodiment (22) the electrode layer can comprise interdigitating left and right electrodes having a tails that comprise repeating wave patterns (e.g. sinusoidal waves). Whether linear or waved shaped, the left and right electrode tails are preferably substantially parallel. Compared to the electrode with the stripe shaped tail (20), the electrode with the wave-shaped tail (22) or 'wavy'-shaped tail is preferred as it has minimum resistance change to stretching, and generates the least interference on the sensor signal. Accordingly, the signal collected with the wavy shaped electrode may provide increased accuracy. Additionally, the wavy shape electrode tail is more resistant to the strain which helps to decrease the strain sensor failure rate. Other types of non-linear shaped electrode tails are possible, including other wave shapes, such as square, triangular or sawtooth wave shapes in particular.

FIG. 2B(ii) shows photographs of the electrodes of FIG. 2B(i) with the application of a sensing layer (28), followed by the application of a hot-melt adhesive based encapsulation layer. The presence of the hot-melt adhesive based encapsulation layer can be detected by way of the change in lustre of the electrodes—from 'shiny' in FIG. 2B(i) compared to those encapsulated in FIG. 2B(ii) having more a 'matt' (non-shiny) appearance.

The overall dimensions of a sensor according to the present disclosure may be adjusted to suit a given application. In embodiments, the overall length of the sensor may span the width of a surface, such as a mattress (e.g. for a single bed or larger). In other embodiments, using the sensor shown in FIG. 2B as an example, the sensor is generally elongate (i.e. long in relation to width). The length of a sensor, from the top of the interdigitated head portion (exemplified by reference 29*a*) to the end of the tail portions (exemplified by reference 29*b*), is from about 2 cm to about 10 cm, preferably about 4 cm to about 8 cm. In embodiments, the overall width of the sensor (exemplified by reference 29*c*) is preferably from about 0.5 cm to about 5 cm, further preferably about 1 cm to about 3 cm. In embodiments, the length of tail portion (exemplified by reference 29*b*) of each electrode (whether straight or incorporating repeating waves) is preferably from about 1 cm to about 8 cm, preferably about 3 cm to about 6 cm. Additionally, the length of head portion of an electrode (exemplified by reference 29*a*) is preferably from about 1 cm to about 8 cm, preferably about 3 cm to about 6 cm. Together, the interdigitated head portions of the left and right electrode define a head region (29*c*), and together the corresponding substantially parallel tail portions of the left and right electrode define a tail region (29*d*).

In embodiments, the width of the track an electrode tail is preferably from about 0.01 cm to 1 cm, further preferably about 0.1 cm to about 0.5 cm. The thickness of an electrode (i.e. the height of electrode comprising head and tail portions as measured from the surface of the substrate to which the electrode is applied) is preferably about 800 nm to 500 μm, further preferably from about 1 μm to about 100 μm, even further preferably from about 10 μm to about 50 μm.

The length of each digitation in the head portion of an electrode (e.g. in head portion marked 29*a* in FIG. 2B) is from about 0.5 cm to 2 cm, preferably from about 0.8 to 1 cm. Further, the width of each digitation is preferably from about 200 μm to 2,000 μm, further preferably from about 500 μm to 1,000 μm.

In embodiments, the amplitude of a wave in each electrode tail is preferably from about 0.5 mm to 50 mm, further preferably from about 1 mm to 10 mm.

In further embodiments, the sensor comprises: a head region defined by the interdigitated head portions of the first and second electrode, and a tail region defined by the tail portions of the first and second electrode. As such, the ratio of electrode head region length to electrode tail length is preferably from about 1:1 to 1:300; further preferably from about 1:3 to about 1:30, even further preferably from about 1:3 to about 1:10. In other embodiments, the ratio of the width of the head region to the width of the tail region (i.e. the width spanning the first and second electrode tails, as exemplified by reference 29*c* of FIG. 2B for example) is between about 1:1 to about 1:3, preferably about 1:1.

In embodiments, the sensing layer size is proportional to the number and length of the digitations in the interdigitated head portion of the sensor. In embodiments, the width of the sensing layer is from about 0.5 to 5 cm, preferably about 1 cm to 3 cm. In embodiments, the length of the sensing layer is from about 0.5 to 5 cm, preferably about 1 cm to 3 cm. In further embodiments, the sensing layer is confined to the head of the sensor, preferably the digitations of the interdigitated head portion of the sensor.

Advantageously, the confinement of the sensing layer to the head portion of an elongate sensor substantially reduces sensor signal variability, and maximises signal to noise ratio. The thickness of the sensing layer is preferably from about 500 nm to 100 μm, further preferably from about 1 μm to about 20 μm.

As a further advantage, and in contrast to conventionally designed electrode-based thin-film pressure sensors, the strain sensor of the present disclosure provides an interdigitated electrode layer in direct contact with the sensing layer without the need for a spacing dielectric (or insulating layer(s)). Thus, according to embodiments, the strain sensor of the present disclosure excludes a dielectric layer between the electrode and sensor layers. This avoids the requirement for an extra alignment step during manufacture which therefore further simplifies the scalable screen-printing process and reduces the sensor production cost.

Figure 2C:
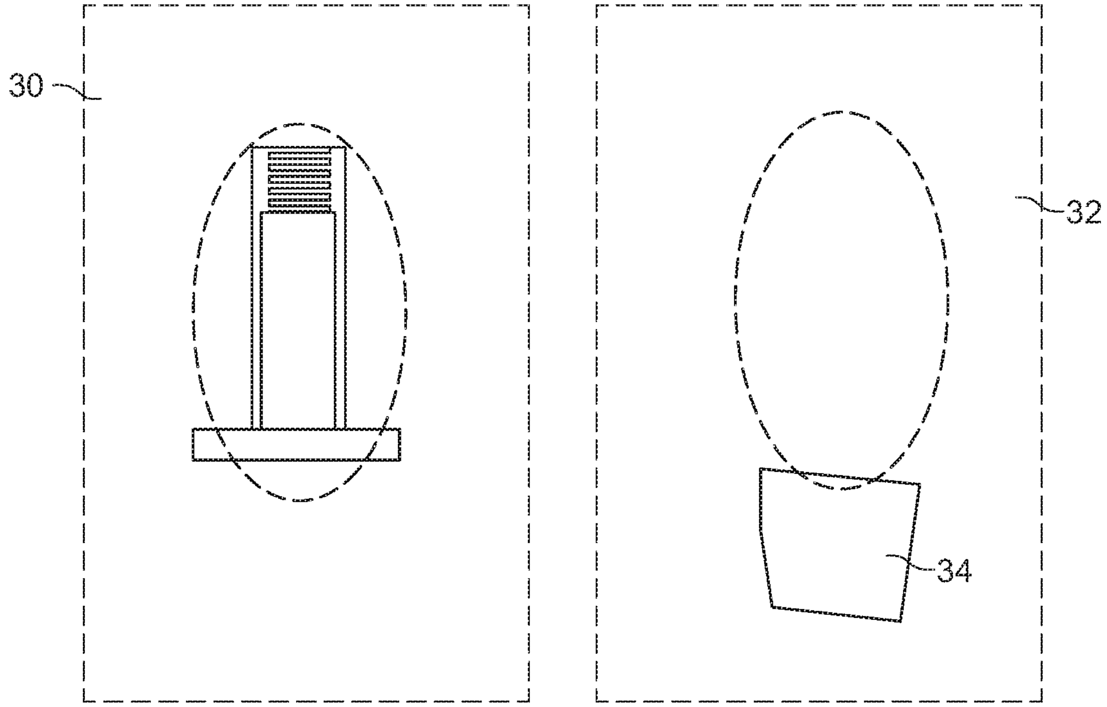
FIG. 2C provides photographs of the electronic strain sensor embedded in mattress cover according to an embodiment of the present disclosure (left) where the dashed line is indicative of the position of the strain sensor from the top surface of the mattress cover (top left) and the reverse side of the mattress cover (bottom left); and the typical resistance change when external pressure applied to the strain sensor embedded in the mattress cover (right).
Figure 2C:
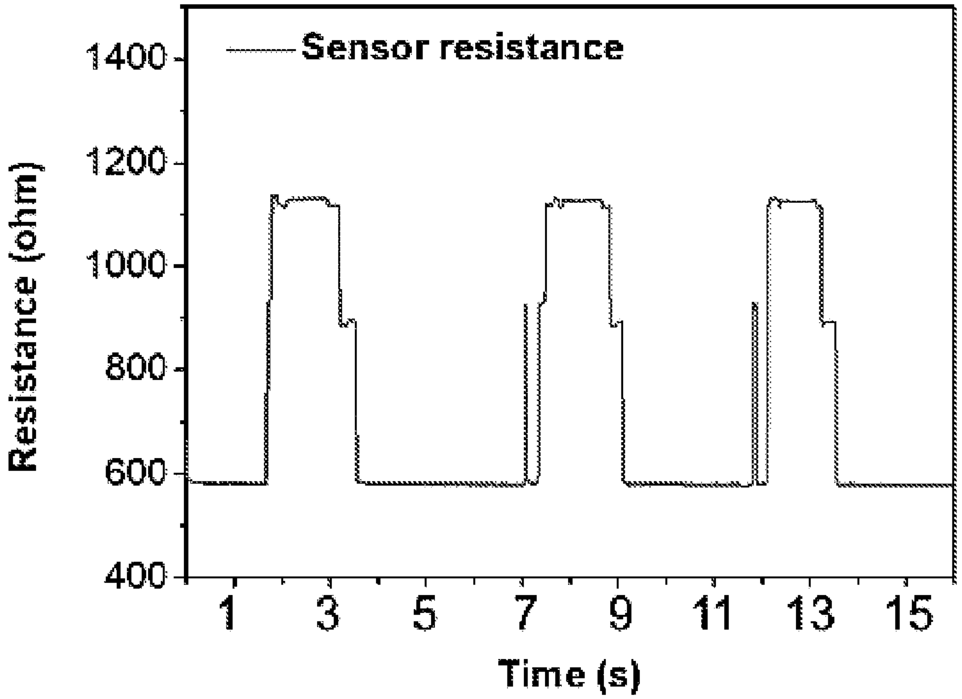

According to embodiments, after the sensor is printed, a hot-melt based transferring technology can be applied to attach the sensor onto an item or device for use in measuring at least one physiological parameter of a living subject. In a preferred embodiment, a hot-melt based transferring technology is used to transfer the strain sensor of the present disclosure to a fabric, thus providing an integrated sensor. Further preferably, the fabric is a mattress cover. In embodiments, the sensor is positioned between layers of a fabric comprising at least two layers. That is, the sensor is integrated within layers of the fabric. FIG. 2C(i) shows an embodiment of a strain sensor of the present disclosure between two layers of fabric (30). In the left panel of FIG. 2C(i), a layer of the fabric layer is removed to assist visualisation of the sensor which is encircled by the dashed lines. The sensor in this embodiment is attached to a substrate with paper lining removed, and hot-melt adhesive and sensing layers facing down. Heat is applied to melt the adhesive layer to enable attachment to the fabric. The sensor is not visible when the fabric is turned over (32), albeit that the dashed line and adhesive tape (34) indicate the position of the sensor. Wires may be connected to the sensor by clip-based connectors, the wires being connected to a control box for signal readout.

The sensor performance test shown in FIG. 2C(ii) shows signal generated by the flexible strain sensor of FIG. 2C(i) when pressure is applied (e.g. when the body of a living subject is sitting or lying on top of the sensor). The sensor can detect any body motions by giving the corresponding resistance change when operating at a low voltage of about 0.001 V to 3 V, preferably about 0.01 V to about 1 V, further preferably about 0.01 V.

In embodiments, in an alternative to a mattress cover, the strain sensor of the present disclosure may be incorporated in any item designed to support the body weight of a living subject, or a portion thereof. For example, a strain sensor of the present disclosure may be incorporated, preferably integrated, into a cover for furniture such as a chair (such as a recliner), a cushion, or a pillow.

Figure 2D:
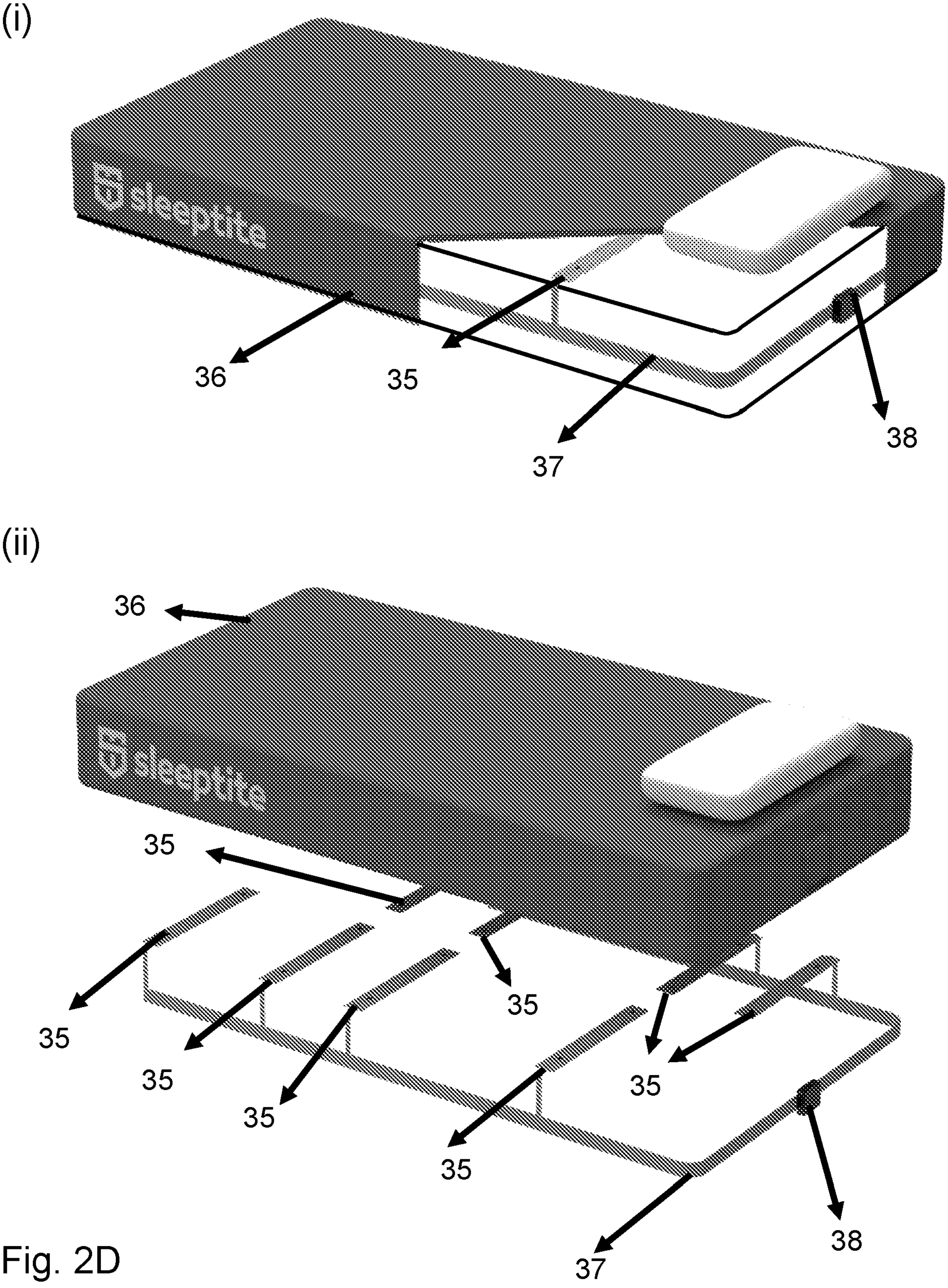
FIG. 2D(i) illustrates one embodiment of an arrangement of an electronic strain sensor of the present disclosure in a mattress cover. A cross section of a portion of the cover showing the sensor and wiring is shown.

In embodiments, at least one sensor may be incorporated into a fabric. FIG. 2D(i) illustrates one embodiment of such a sensor arrangement. The strain sensor (35) may be incorporated onto a surface of a mattress cover (36)—a portion of the mattress cover (36) that is cutaway revealing the integrated sensor (35) is shown. Incorporation may be by way of a hot melt adhesive as previously described to the inner surface of the mattress cover, or between at least two layers of a mattress cover. Alternatively, other adhesives (e.g. fabric glue) or attachment method (e.g. sewing or Velcro™ fastener) may be employed. The figure shows the sensor connected by one or more wires (37) to a control box (38). In alternative embodiments, a fabric may comprise an array of flexible sensors according to the present disclosure.

FIG. 2D(ii) shows an example of an array arrangement. Specifically, the figure provides an exploded view of an array of sensors (35) integrated into a mattress cover (36), with one or more connecting wires (37) and a control box (38). Preferably, as shown in FIG. 2D(ii) the arrangement of sensors in an array substantially covers a mattress surface.

It has been found that the sensing mechanism of the strain sensor according to the present disclosure is correlated with the formation of microscopic cracks (or 'micro-cracks') within the sensing layer when under pressure. That is, when external force is applied to or near the sensor, flexing and/or stretching of the sensor causes the generation of micro-cracks within the thin film of the sensing layer, which induces an increased resistance. Once the pressure/strain is relieved, the elastic polymer matrix within the sensing layer, the elastomeric properties of the electrode layer, substrate and hot-melt layer, or combinations thereof, substantially eliminates the cracks and restores a continuous sensing layer, which leads to the recovery (i.e. reduction) of resistance. In this regard, the sensor of the present disclosure is both flexible and stretchable enabling improved accuracy of detection of external forces compared to existing non-flexible sensors, or sensors which are flexible but no stretchable.

Figure 3:
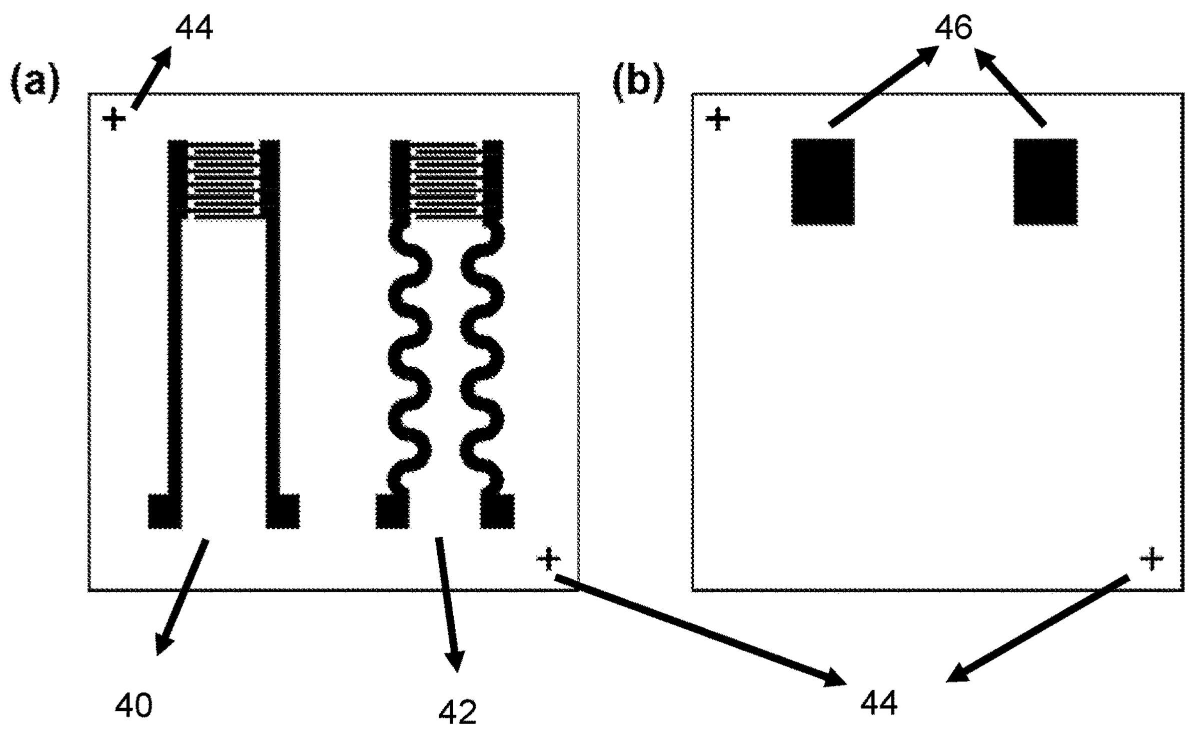
FIG. 3 (*a*) illustrates screen mask designs of the interdigitated electrode patterns according to an embodiment of the present disclosure.

As described above, in embodiments, two patterns may be printed to create a strain sensor according to the present disclosure. An interdigitated pattern for electrodes and a rectangular pattern for the sensing layer. FIGS. 3 (*a*) and (*b*) illustrate mask designs according to an embodiment of the present disclosure. FIG. 3 (*a*) illustrates a mask design for a sensor having a 'linear' electrode tail (40) next to an electrode having a 'wavy' electrode tail (42)—in production, a mask would preferably comprise a sensor having only one type of tail design. FIG. 3 (*b*) illustrates a mask for the sensing layer (46) which is subsequently overlaid onto the printed electrode layer. Masks of the present disclosure, preferably include cross '+' marks (44) created in the corners to facilitate alignment when printing of two layers, thus achieving better printing resolution.

For masks, a stainless steel type having about 60-130 thread/cm stainless steel thread is preferred. Further preferably, an ink emulsion layer thickness of about 20-40 μm is applied using the masks. However, other types of masks may be used, including a polyester screen having about 50-100 thread/cm for example, preferably with a similar emulsion layer thickness.

For interdigitated-patterned electrode layer printing, a commercially available ink which contains Ag particles, ethyl acetate, butyl acetate and isopropyl acetone could be used. For example, EDAG 725A (LOCTITE®, HENKEL), EDAG 478SS (LOCTITE®, HENKEL) and POLU-10P (SP130®, SHENZHEN POWER LUCK INK), or combinations thereof, are suitable. Other alternative inks that are suitable for flexible device printing may be used. Preferably, an ink (whether a single ink or a blend of inks) suitable for printing the electrode layer has a sheet resistance at a 25 μm thickness of less than 10 ohms, preferably less than 1 ohm, further preferably less than 0.015 ohms. Preferably, the sheet resistance of the electrode layer at a 25 μm thickness is about 0.001 to about 0.02 ohms, most preferably about 0.015 ohms.

For the sensing layer printing, a commercial ink that shows fast responsive sensitivity profiles to applied force is preferred. The ink may contain carbon black, graphite, epoxy, ethyl acetate, isopropanol, butyl acetate and isopropyl acetone. For example, an ink prepared from a mixture of ECI-7004-LR (LOCTITE®, HENKEL), a carbon-containing thermoplastic conductive ink, and NCI-7002 (LOCTITE®, HENKEL), a carbon-containing thermoplastic non-conductive ink, is preferred. As such, in embodiments, the ink for printing the sensing layer comprises a blend of a conducting ink and a non-conductive ink to provide a desired resistivity. Further preferably, the ratio of ECI7004-LR:NCI-7002 may be in a range of about 1:100 to about 100:1, more preferably about 1:10 to about 10:1. In an alternative embodiment, a range of about 2 to about 6 parts in 10 of ECI7004-LR in a ECI7004-LR and NCI-7002 mixture may be used. Mixtures of these inks at a range of volume ratios can be used to achieve a resistance range from about 100 to about 10,000 ohm, for example as shown in Table 1.

TABLE 1

Sheet resistivity

Blending ratios of LOCTITE ECI 7004LR and LOCTITE NCI 7002, Dried 5 minutes @ 120 °C, ohms/sq

| LOCTITE ECI 7004LR (% by weight) | LOCTITE NCI 7002 (% by weight) | @ 25 μm dry coating thickness |
|---|---|---|
| 100 | 0 | 35 |
| 90 | 10 | 50 |
| 80 | 20 | 70 |
| 70 | 30 | 105 |
| 60 | 40 | 170 |
| 50 | 50 | 290 |
| 40 | 60 | 675 |
| 30 | 70 | 2160 |
| 25 | 75 | 4500 |
| 20 | 80 | 35,000 |
| 10 | 90 | >1e9 |

Other alternative force sensitive inks can also be used for this application, such as CI-2001 (Nagase Chemtex®; having a resistance of 50 ohms at a thickness of 10-20 μm) and CI-2050LR (Nagase Chemtex®; the resistivity of which is adjustable by blending with CI-2050 HR), or combinations thereof. In embodiments, an ink (whether a single ink or a blend of inks) suitable for preparing the sensing layer comprises a sheet resistance at a 25 μm thickness is at least 20 ohms, preferably at least 100 ohms, more preferably at least 1,000 ohms, even more preferably at least 100,000 ohms.

Ink mixing may preferably be performed by using a vacuum mixer (THINKYMIXER® ARV-310LED) to avoid any air bubbles, where the ink is used immediately after preparation to avoid any possible sedimentation. For longer shelf time, the original ink stock may be stored in a 4° C. fridge with sealed cap.

Substrate and Adhesive Materials Selection and Preparation

In embodiments, a thermoplastic PU ester grade film cat no. FS1155 (DINGZING® Advanced Materials Inc., having properties of item 3 of Table 2) is preferred as the printing substrate. Compared to other materials, the FS1155 film has a relative high melting point (about 150° C.). This temperature is preferable to support ink drying above ambient temperatures. FS1155 also has excellent stretchability (>600%) which enables its application in making sensors according to the present disclosure. Further to this, such material is waterproof and does not generate any noise when the film is ruffled. All the features mentioned above also make this PU film a preferred candidate for manufacturing electronics circuits on fabric.

Figure 4A:
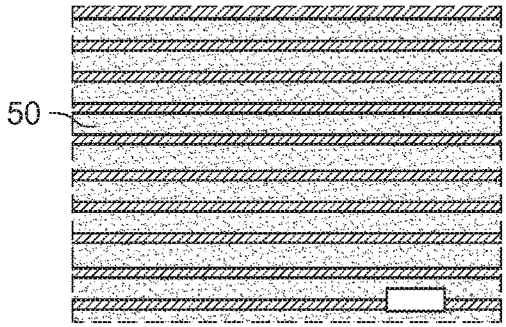
FIG. 4 (*a*) shows optical microscopy images of the printed electrodes (reflection mode) according to an embodiment of the present disclosure; scale bars are 1.5 mm and 500 μm for low (left images (i) and (iii), white scale bar) and high (right images (ii) and (iv), black scale bar) magnification, respectively.
Figure 4B:
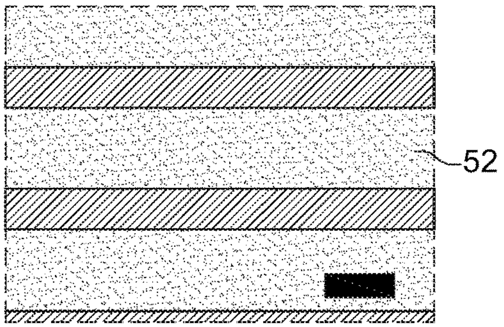
Figure 4B:
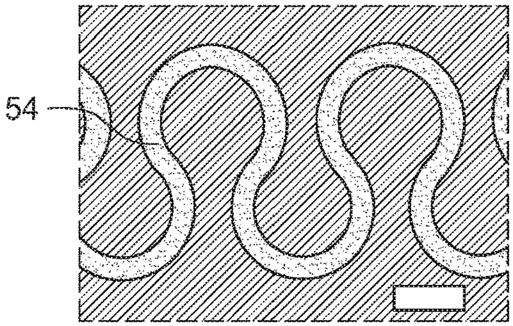
Figure 4B:
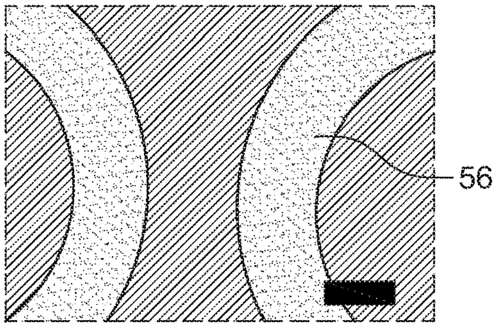
Figure 4B:
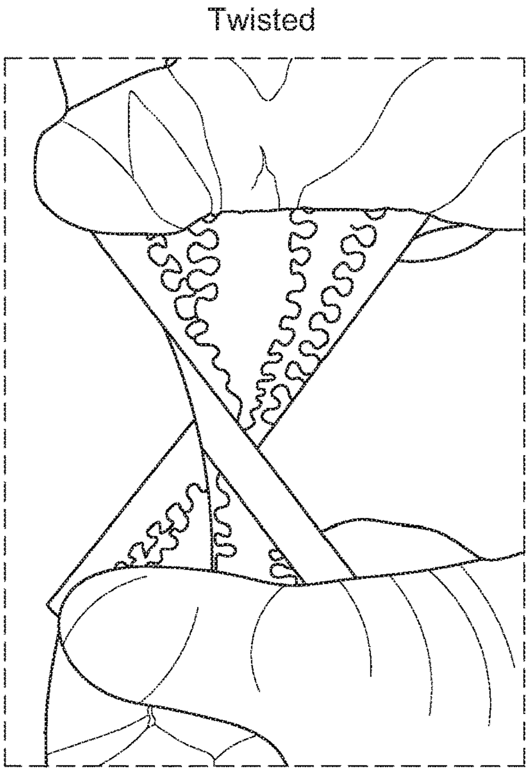
Figure 4:
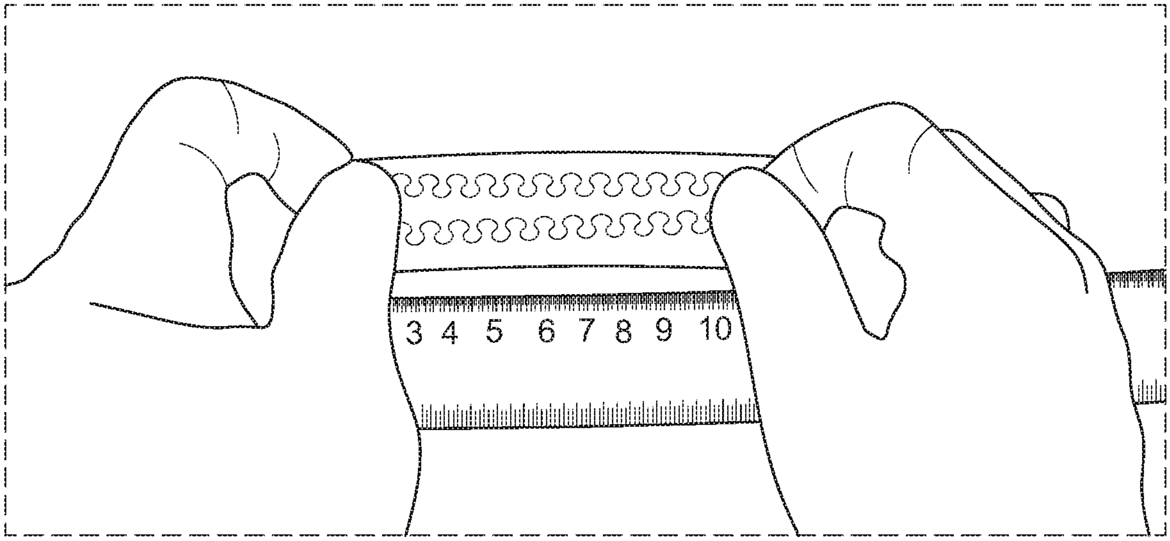
Figure 4:
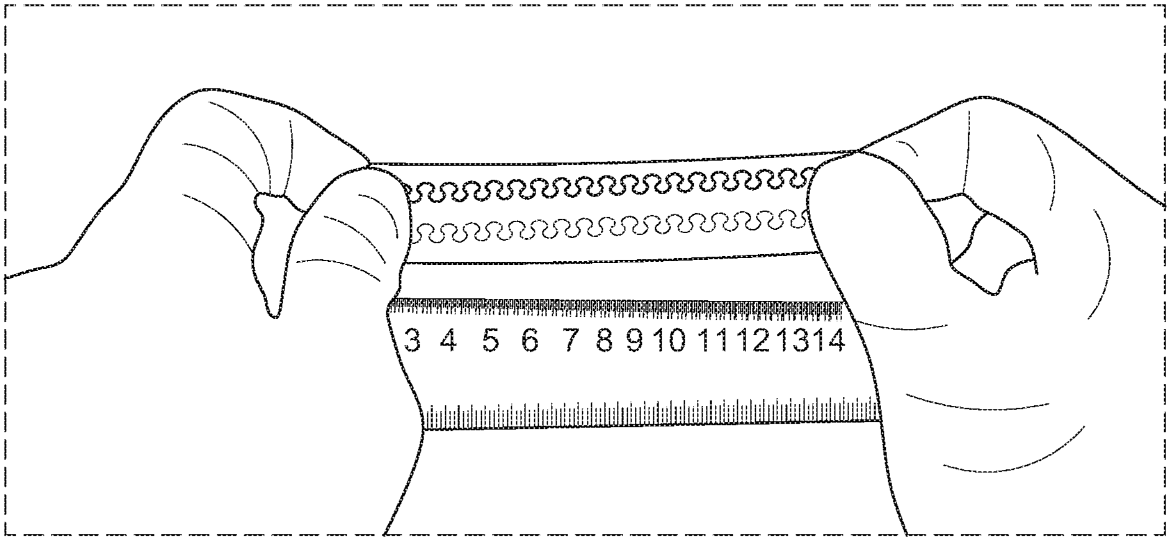

Regarding printed film stretchability and durability, FIG. 4 (*a*) (i)-(iv) shows optical microscopy images of printed and encapsulated electrodes according to embodiments of the present disclosure, where scale bars are 1.5 mm for low (Figs (i) and (iii), white scale bar) and 500 μm for high (Figs. (ii) and (iv), black scale bar) magnification images. Straight, parallel printed electrode lines at low (50) and high (52) magnification, and wavy line-printed electrodes (in a more prominent 'river-bend' type loop pattern) at low (54) and high (56) magnification are shown. FIGS. 4 (*b*) and (*c*) show that the printed film can undergo vigorous manipulation (e.g. stretching, bending and/or twisting). This manipulation does not impact functioning of the electrode. FIG. 4 (*c*) (i) and (ii) compare a printed electrode under no strain versus 30% strain, respectively. Accordingly, in embodiments, a substrate with a printed electrode can sustain between about 10% to about 80% strain without impacting electrode function, further preferably a substrate with a printed electrode can sustain between at least 30% strain without impacting electrode function.

In embodiments, a 150 μm thick PU film with paper release liner as a substrate is preferred as it provides excellent handling characteristics for the strain sensor manufacturing process of the present disclosure. The PU sheet can be used directly without further modification, according to one embodiment. However, the PU sheet can be further modified if needed according to other alternative embodiments.

In embodiments, a hot melt adhesive sheet cat no. FS3258 (DINGZING® Advanced Materials Inc., having the characteristics of item 10 of Table 2) is preferred to create the encapsulated sensor of the present disclosure. The hot melt adhesive sheet includes at least one of thermoplastic polyurethane-ester, lubricant and UV absorber, and has a melting point of about 85° C.

The FS3258 hot melt adhesive sheet melts under high temperature heating and bonds to most surfaces once it cools to ambient temperature. In addition, the sheet does not lose its thickness after solidifying which makes it a good candidate for both adhesion and encapsulation. In an embodiment, to transfer the FS3258 sheet onto the ink-coated FS1155 PU sheet, a heat press machine (MORPHORN® Heat Press, 12×15 inch, equivalent to about 30.5×38.1 cm) is used. Generally, any heat press or emitting device that can provide up to about 120° C. heating under pressure, and comprises an operating stage that can fit the printed sensor, could be used to transfer the FS3258 sheet onto the PU sheet.

Screen-Printing and Assembling of the Sensing Layer

According to an embodiment, an automatic screen printer (RT06001, Pacific Trinetics Corporation®) is used for the fabrication of the electronic sensor. The RT06001 can print a sheet below 6"×6" (15.24 cm×15.24 cm) square and can adopt a screen with the frame size of 320 mm×320 mm square, and 15 mm high. To start the electrode layer printing process, a FS1155 PU substrate with paper liner is first placed firmly on the stage of the RT06001 by vacuum suction. Then the patterned mask for printing the electrode (e.g. as shown in FIG. 3 (*a*)) is then fitted onto the printer. An Ag-based ink is then poured onto the mask on the edge near to the squeegee. Preferably, the ink needs to be placed in a rectangular shape covering the full width of the squeegee with relative even thickness. Once everything is in position, printing is then started. A blading process pushes the ink liquid to cover whole printing area, followed by application of pressure with a squeegee to complete the printing. The substrate is then released by removing the vacuum suction and transferred onto a flat metal pad for drying. In a continuous production method, a new substrate could be fitted onto the stage to repeat the printing. Roll-to-roll production can be realised with alterations to the printer. Unused Ag ink is collected, and the mask is cleaned with acetone/isopropanol once finished. To cure the Ag ink on PU sheet, the substrate is placed into an oven at about 80° C. for approximately 15 minutes. Alternatively, approximately 25 minutes or more drying under ambient (room temperature) conditions is sufficient to enable ink drying.

A second step comprises printing the sensing layer onto the cured substrate. A dedicated mask, such as a rectangular design (e.g as shown in FIG. 3 (*b*)), is installed followed by placing a blank PU sheet onto the printer stage with vacuum suction. Similarly, pre-mixed carbon ink is then placed onto the mask. A test run may be performed to check the positions of the cross marks on the sheet before printing. A built-in camera can be used to align the camera marker position with the test-printed cross mark position. Once this alignment process is complete, the camera marker location can be locked. The cured substrate comprising a printed electrode is then placed onto the printer stage to match the cross mark positions with camera marker. Printing is then started, with a blade pushing ink followed by application of the squeegee. The printed sensor is then transferred for curing by heat as described above. The connectors are then attached onto the circuit port using the commercially available crimp flex connectors (For example: CJT, A2550-TP-CR, 2.54 mm pitch FFC crimp flex connector, Nicomatic CRIMPFLEX® 2.54 mm pitch connector system) to ensure the stable connection.

A third step comprises encapsulation. Encapsulation protects the printed circuits from oxidisation and breakage under stain, while also contributing to the stretchability and resilience of the sensor. A hot-melt layer is cut with a desired shape and then placed on top of the printed sensor, followed by placing the combined sensor and hot-melt layer into a heat press machine (MORPHORN® Heat Press, 12×15 Inch). Heat is applied at about 105° C. for approximately 50 s under pressure from about 50-60 PSI. The combination is then cooled to room temperature to complete the encapsulation process.

The final step comprises transferring the printed electronic sensor onto a surface, particularly a cover fabric (i.e. a mattress cover fabric). The heat press machine is preheated to about 105° C. The encapsulated electronic sensor device is placed onto the desire location on backside of the cover fabric. It should be understood that the encapsulation layer side needs to be in contact with the back side of a cover with the paper liner facing up. Once the position is confirmed, the hot press is applied (MORPHORN® Heat Press, 12×15 Inch, about 50-60 PSI). After about 50 s heating and applying pressure, the whole electronic sensor device is transferred onto the cover. Apart from mattress covers, application of bonding the sensors can be given to any material through high temperature, more specifically through heating at 105° C.

Sensor Performance

Figure 5:
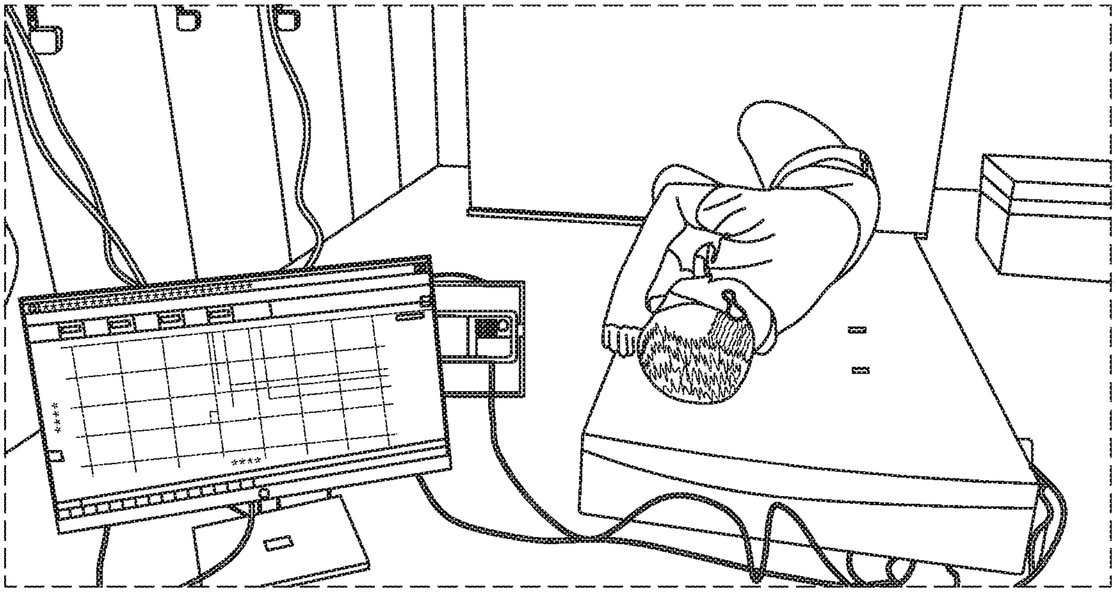
FIG. 5 (*a*) is a photo of an embodiment of a non-invasive monitoring system of the present disclosure where strain sensor testing is depicted using a source meter and a user laying and moving on top of a strain sensor embedded in a mattress cover.
Figure 5:
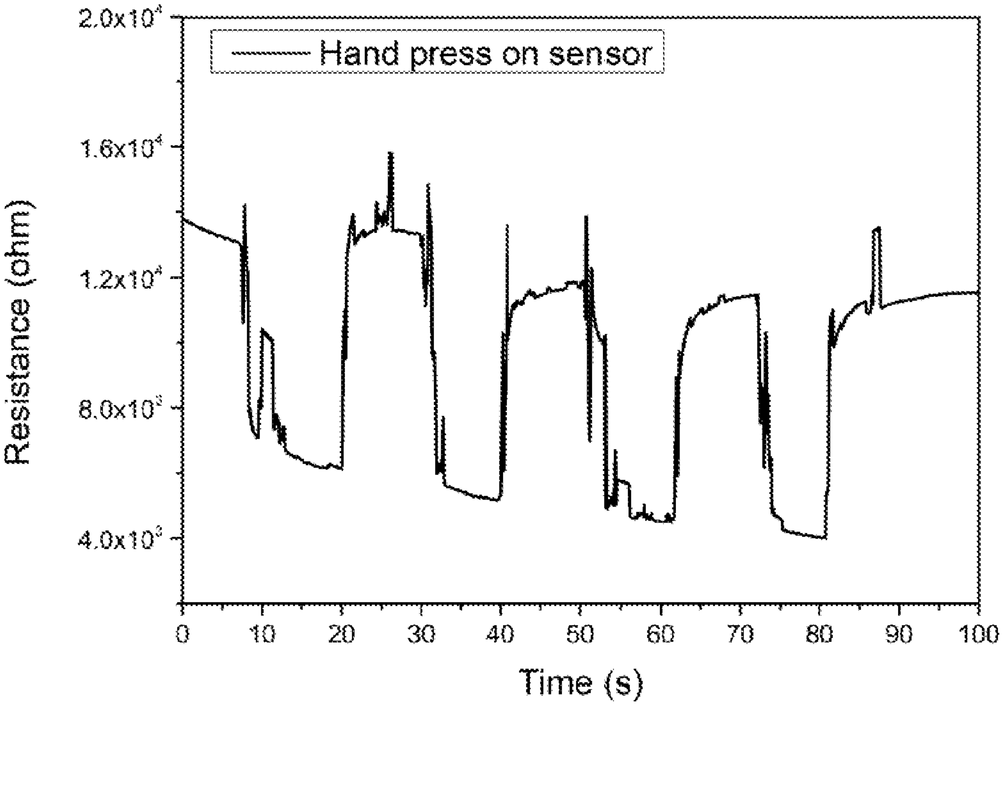
Figure 5:
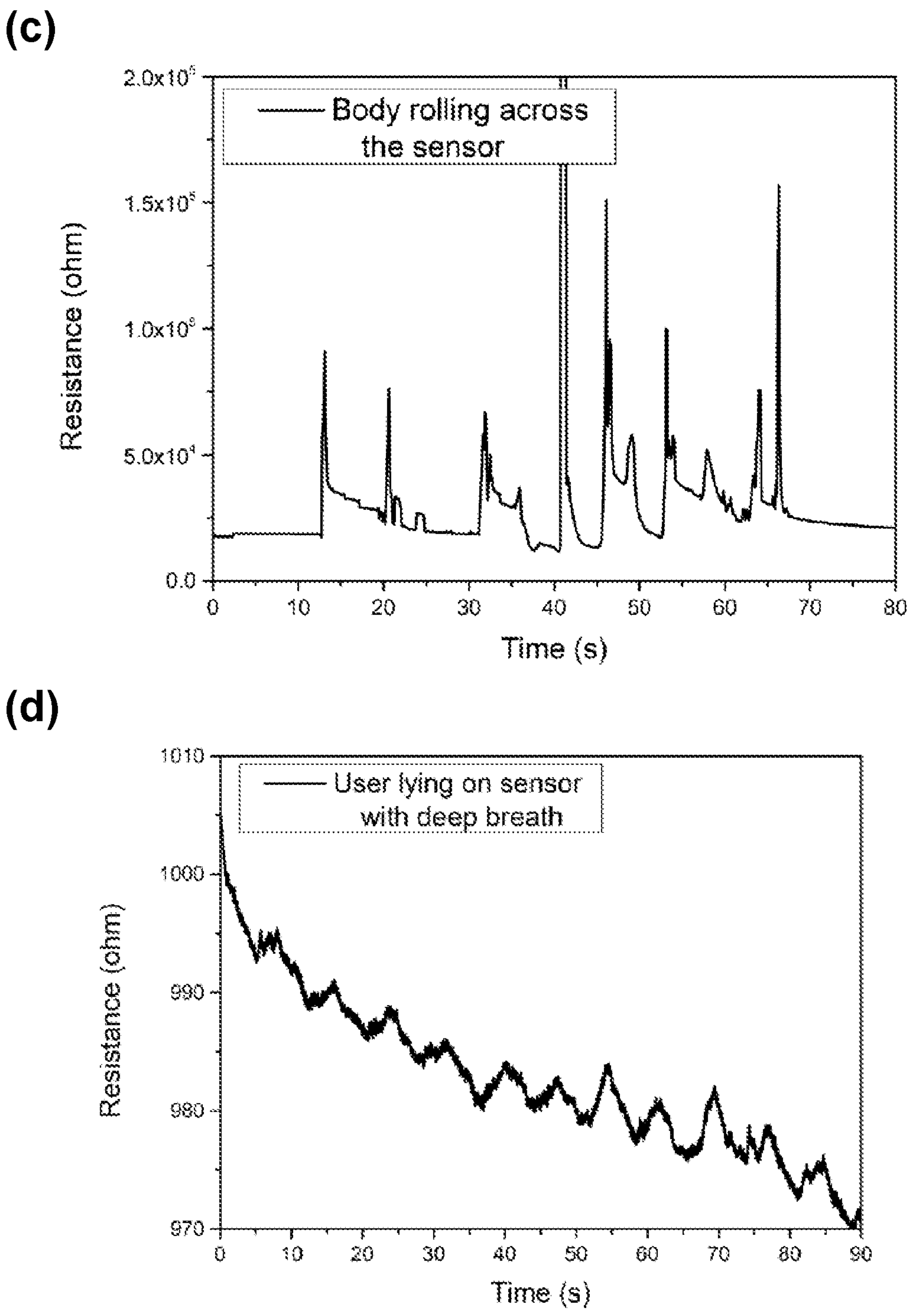
Figure 5:
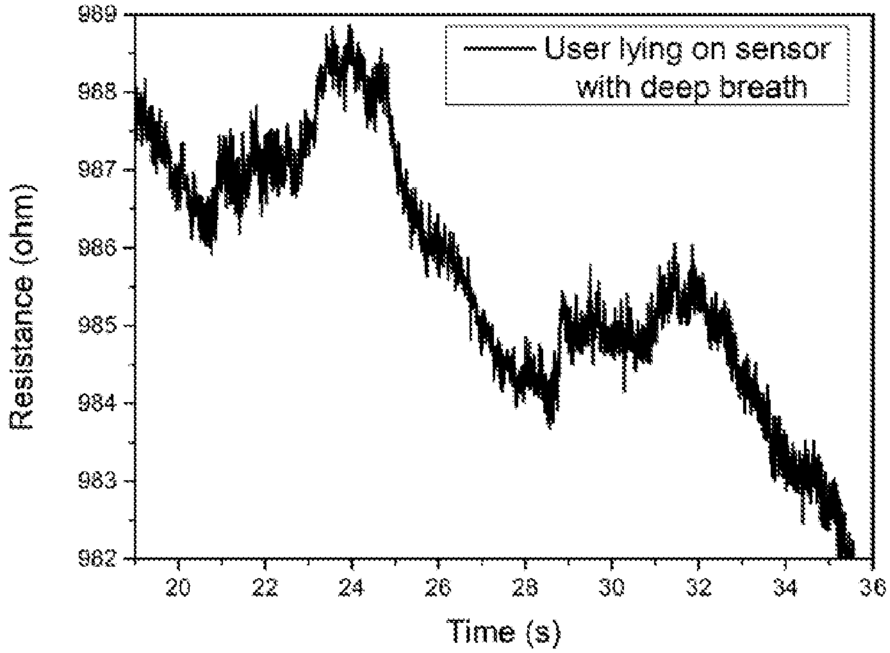

In embodiments, sensor performance is evaluated by connecting the flexible sensor with a source meter. With an operating voltage at 0.01 V, a fingertip press, hand press, body weight pressure, body motion as well as deep breath can be detected by the flexible sensor. FIGS. 5 (*a*)-(*e*) show an example of a testing system and associated testing results for a strain sensor according FIGS. 2 and 3 which is embedded in a mattress cover. FIG. 5 (*a*) shows the system which comprises a strain sensor embedded in a mattress cover, a test subject laying on the mattress, a source meter and computer readout. The resistance profile generated by repetitive hand presses is shown in FIG. 5 (*b*), whereas FIG. 5 (*c*) shows the resistance profile a subject's body movement. FIGS. 5 (*d*) and (*e*) show the resistance profiles generated by a subject lying still on the mattress-embedded sensor, where the subject is breathing deeply. These data clearly demonstrate that the strain sensor made according to the present disclosure is sensitive, and can detect slight motions on the mattress through the resistance changes. That is, when there is any external pressure change on the mattress, that pressure is applied to the sensor which then generates micro-cracks within the sensing layer. Depending on the amount of the cracks that occur, the resistance of sensors will then increase proportionately. Once the external pressure is released, the elasticity of the various components of the sensor (substrate, inks, and encapsulation layer) drives the sensor to recover to its initial state and merges the micro-cracks back to a continuous layer. This enables a decrease in resistance.

Durability Testing

A durability test may be performed on sensors, control box and wiring harness. In an embodiment, the sensors are transferred onto a mattress cover and then placed on top of a mattress that is subjected to mattress rollator testing. Rollator testing for a mattress (such as that governed by American Society for Testing and Materials (ASTM) standard F1566) measures characteristics including mattress firmness retention and surface deformation. The testing may be performed at various cycle points (typically from about 0 to about 100,000 cycles) to simulate mattress performance over 10 years of use by a subject between about 80 to about 130 kg, in body weight preferably a subject of about 120 kg in body weight. Rollator testing therefore provides one mechanism for validating the robustness of the sensors.

Figure 6:
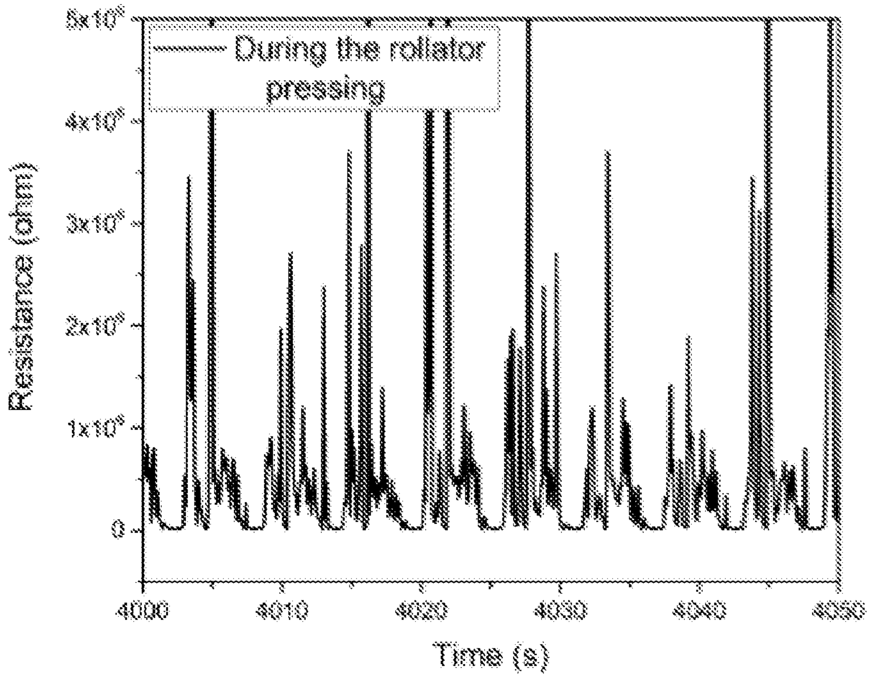
FIG. 6 (*a*) illustrates the resistance curve generated by an embedded strain sensor in a mattress cover according to an embodiment of the present disclosure, where the mattress is undergoing rollator testing.
Figure 6:
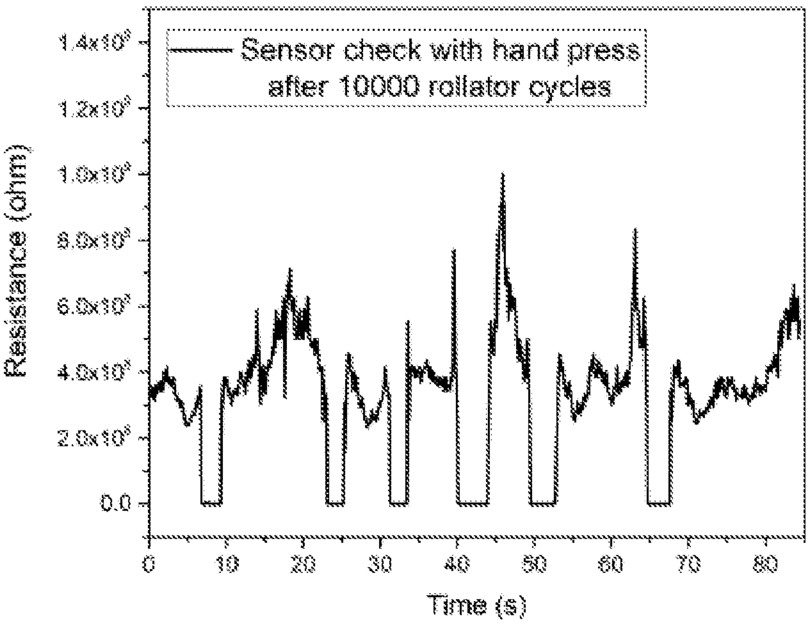

FIG. 6 shows the resistance profiles of a rollator test for a mattress covered with a cover comprising an embedded flexible and stretchable strain sensor according to the present disclosure. FIG. 6 (*a*) shows changes in resistance during a rollator test where resistance changes according to the proximity of the rollator to the sensor, as expected. FIG. 6 (*c*) shows a hand press test on a mattress covered with a cover comprising an embedded strain sensor, where the covered mattress had previously undergone testing with 10,000 rollator cycles. The figure shows that repetitive hand presses are consistently recognised, inferring that the sensor was not damage as a consequence of the rollator testing. These data show that flexible and stretchable strain sensors according to present disclosure have an equivalent durability of many years in the face of general wear and tear.

In further embodiments, durability testing for the PCB, control box and wiring harness may include testing sensitivity and robustness at varying temperatures, different levels of humidity, dust resistance, water resistance (e.g. high pressure jets, water dripping), and against mattress toppling, shock, vibration, packaging and shipping. Sensors may also undergo similar testing.

Data Generation and Communication

Figure 7:
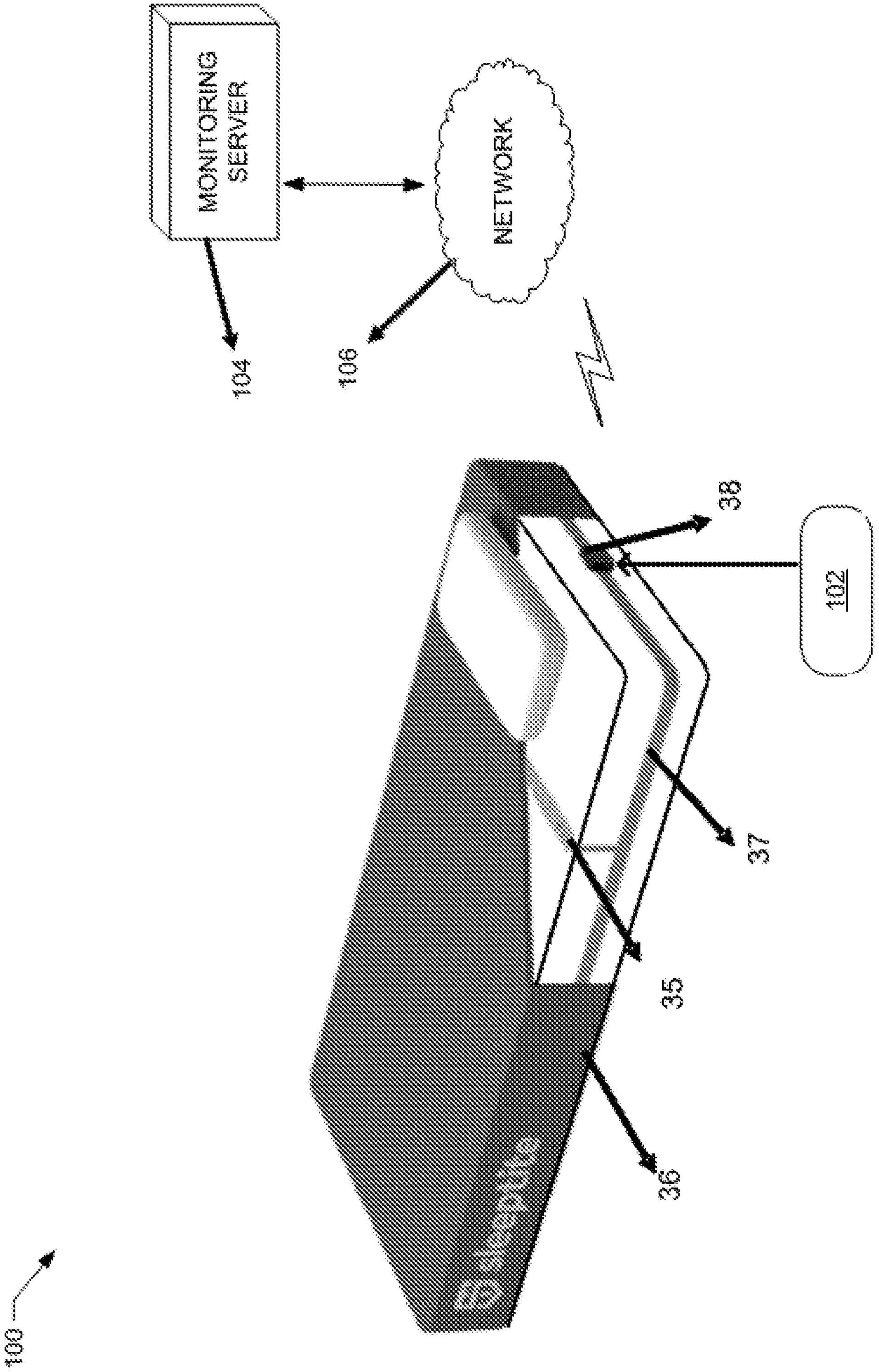
FIG. 7 shows an example of a monitoring system, according to an example embodiment of the present disclosure.

According to an embodiment, there is provided a non-invasive monitoring system. FIG. 7 shows an example of such a monitoring system (100), which comprises a flexible array of strain sensors (35) integrated into a mattress cover (36), with one or more connecting wires (37) and a control box (38). The control box (38) is electrically connected to a power supply (102), which may include any AC or DC voltage source. For example, the power supply (102) may include a wall outlet and the control box (38) is connected via a power cord. In other examples, the power supply (102) may include a battery. The control box (38) may be connected to the battery via a power cord. In other embodiments, the power source (102), such as a battery, may be integrated with the control box (38).

The control box (38) may include a wireless communication unit that is communicatively coupled to a monitoring server (104) via a network (106). In some embodiments, the control box (38) is wirelessly coupled to the network (106) via a Wi-Fi® access point or gateway. In other embodiments, the control box (38) is wirelessly coupled to a smartphone or tablet computer, which are connected to the network (106) via a wired or wireless connection such as a NFC connection, a Bluetooth® connection, an RFID connection, or a Zigbee® connection. In embodiments, control box (38) may include a resistor, capacitor, I/O expander, NPN transistor, multiplexer, microcontroller, Digital to Analog converter (DAC), memory and connector.

In embodiments, the communication unit of the control unit (38) is configured to store sensed data locally (within the unit or a computer readable medium such as a hard disc or other writable memory) or transmit the data to an external device such as a computer, a mobile device and/or the monitoring server (104) (e.g., a cloud computing server). The data may be visualised in real-time by utilising an external device.

In embodiments, the control unit (38) is configured to send the collected data from the flexible sensor(s) (35) to the monitoring server (104) while providing power to the flexible sensor(s). Additionally, the body movement in real time can be shown in a web-based interface, irrespective of whether the communication unit is wireless or not.

The monitoring server (104) may include any processor, workstation, computer, etc. configured to receive sensed data via the network (106) from the control unit (38). The monitoring server (104) stores the received data to a database in an account associated with the user. The monitoring server (104) includes one or more interfaces to enable a user or a third-party to access (using a smartphone, tablet computer, computer, etc.) the account to graphically view the data. In some instances, the monitoring server (104) may use one or more thresholds to detect when and/or how much a user moved and create one or more data visualizations showing how a user moved during sleep or rest.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

TABLE 2

Properties of Suitable Hot-Melt Films

| Item | Hardness (Shore A/D) ASTM D2240 | Specific Gravity ASTM D792 | Tensile Strength (kg/cm$^2$) ASTM D412 | Tear Strength (kg/cm) ASTM D624 (Die C) | 300% Modulus (kg/cm$^2$) ASTM D412/D882 | Elongation (%) ASTM D412/D882 | Melting Point (° C.) | Features & possible Applications |
|---|---|---|---|---|---|---|---|---|
| 1 | 82A | 1.2 | warp: 501<br>weft: 542 | warp: 70<br>weft: 71 | warp: 79<br>weft: 76 | warp: 623<br>weft: 632 | 115 | Clear technical film<br>Easy to be worked with high frequency welding<br>Shoes and other accessories<br>Good to bond with fabric and non-woven fabric<br>Processing for apparel |

TABLE 2-continued

Properties of Suitable Hot-Melt Films

| Item | Hardness (Shore A/D) ASTM D2240 | Specific Gravity ASTM D792 | Tensile Strength ($kg/cm^2$) ASTM D412 | Tear Strength (kg/cm) ASTM D624 (Die C) | 300% Modulus ($kg/cm^2$) ASTM D412/D882 | Elongation (%) ASTM D412/D882 | Melting Point (° C.) | Features & possible Applications |
|---|---|---|---|---|---|---|---|---|
| 2 | 55A | 1.13 | warp: 173<br>weft: 181 | warp: 49<br>weft: 54 | warp: 24<br>weft: 240 | warp: 950<br>weft: 963 | 108 | High resilience<br>Low hardness<br>Lingerie<br>Stretch fabric lamination such as activewear |
| 3 | 74A | 1.16 | warp: 343<br>weft: 518 | warp: 45<br>weft: 56 | warp: 193<br>weft: 98 | warp: 383<br>weft: 502 | 150 | High recovery<br>Excellent recovery,<br>Strain Set Rate <3%<br>Soft Stretch fabric lamination such as activewear<br>Good to bond with fabric and non-woven fabric<br>Processing for apparel |
| 4 | 47D | 1.2 | warp: 435<br>weft: 345 | warp: 146<br>weft: 139 | warp: 104<br>weft: 88 | warp: 857<br>weft: 807 | 85 | Stiff Suitable for low temperature process<br>*REACH Approved<br>Digital device accessories, cuff, collar and others<br>Good to bond with fabric and non-woven fabric<br>Processing for apparel |
| 5 | 92A | 1.16 | warp: 88<br>weft: 95 | warp: 62<br>weft: 62 | warp: 56<br>weft: 62 | warp: 524<br>weft: 493 | 50 | Flame retardant hot melt film<br>UL94 V-0 grade<br>Non-halogenated<br>Eco-friendly<br>Solvent-free<br>High elastic<br>Perfect for microfiber fabrics, PU leather, and genuine leather, among other materials |
| 6 | 95A | 1.19 | warp: 342<br>weft: 361 | warp: 106<br>weft: 90 | warp: 121<br>weft: 98 | warp: 866<br>weft: 863 | 60 | Suitable for low temperature process<br>Digital device case wrapping and other genuine leather wrapping<br>REACH Approved<br>Good to bond with fabric and non-woven fabric<br>Processing for apparel |
| 7 | 45D | 1.2 | warp: 542<br>weft: 563 | warp: 149<br>weft: 152 | warp: 111<br>weft: 115 | warp: 769<br>weft: 789 | 85 | Stiff<br>Suitable for low temperature process<br>REACH Approved<br>Shoes, reinforcement and other accessories |
| 8 | 54A | 1.13 | warp: 100<br>weft: 100 | warp: 25<br>weft: 25 | warp: 23<br>weft: 23 | warp: 1026<br>weft: 1008 | 102 | Low hardness<br>Soft<br>Great recovery and extensibility |
| 9 | 67A | 1.16 | warp: 99<br>weft: 99 | warp: 31<br>weft: 31 | warp: 23<br>weft: 22 | warp: 970<br>weft: 978 | 104 | Solvent-free<br>Great recovery and elasticity<br>Soft touch with low hardness<br>Melting point at 100° C.<br>Perfect for microfiber fabrics, PU leather, and genuine leather, among other materials |
| 10 | 72A | 1.19 | warp: 211<br>weft: 211 | warp: 54<br>weft: 54 | warp: 46<br>weft: 46 | warp: 779<br>weft: 778 | 85 | Low melting temperature<br>High viscosity<br>REACH Approved<br>Bra piping<br>Good to bond with fabric and non-woven fabric<br>Processing for apparel |
| 11 | 83A | 1.21 | warp: 383<br>weft: 382 | warp: 75<br>weft: 70 | warp: 73<br>weft: 72 | warp: 717<br>weft: 723 | 113 | Tin-free<br>Plasticier free<br>Hot melt for shoes<br>High elastic<br>Perfect for microfiber fabrics, PU leather, and genuine leather, among other materials |
| 12 | 40D | 1.2 | warp: 389<br>weft: 322 | warp: 105<br>weft: 103 | warp: 82<br>weft: 77 | warp: 796<br>weft: 776 | 65 | Suitable for low temperature process |

TABLE 2-continued

| Properties of Suitable Hot-Melt Films | | | | | | | | |
|---|---|---|---|---|---|---|---|---|
| Item | Hardness (Shore A/D) ASTM D2240 | Specific Gravity ASTM D792 | Tensile Strength ($kg/cm^2$) ASTM D412 | Tear Strength (kg/cm) ASTM D624 (Die C) | 300% Modulus ($kg/cm^2$) ASTM D412/D882 | Elongation (%) ASTM D412/D882 | Melting Point (° C.) | Features & possible Applications |
| 13 | 195A | 1.17 | warp: 475<br>weft: 454 | warp: 93<br>weft: 95 | warp: 78<br>weft: 77 | warp: 768<br>weft: 759 | 82 | REACH Approved<br>Seam sealing tape<br>Digital device case wrapping and other genuine leather wrapping<br>Good to bond with fabric and non-woven fabric<br>Processing for apparel<br>Solvent-free<br>Designed for electronic device case, cell phone case<br>Suitable for heat adhesion with PVC and microfiber |
| 14 | — | 1.18 | warp: 317<br>weft: 379 | warp: 51<br>weft: 47 | warp: 64<br>weft: 65 | warp: 568<br>weft: 563 | High Temp: 145<br>Low Temp: 90 | High recovery,<br>Multiple layer structure<br>Bra, Cup piping |
| 15 | — | 1.18 | warp: 382<br>weft: 486 | warp: 64<br>weft: 61 | warp: 64<br>weft: 62 | warp: 576<br>weft: 611 | Face to non-releasing paper: 116<br>Mid-layer: 160<br>Face to releasing paper: 116 | High recovery, multiple layer structure<br>Waistband<br>Bra wings |
| 16 | — | 1.17 | warp: 451<br>weft: 489 | warp: 48<br>weft: 57 | warp: 85<br>weft: 68 | warp: 488<br>weft: 529 | 115 | OEKO-TEX Approved<br>REACH Approved<br>High resilience<br>Low hardness<br>Lingerie<br>Stretch fabric lamination such as activewear<br>Good to bond with fabric and non-woven fabric<br>Processing for apparel |
| 17 | 160A | 1.19 | warp: 378<br>weft: 286 | warp: 51<br>weft: 63 | warp: 69<br>weft: 37 | warp: 799<br>weft: 803 | 115 | High resilience<br>Low hardness<br>Lingerie<br>Stretch fabric lamination such as activewear |
| 18 | 65A | 1.08 | warp: 30<br>weft: 27 | warp: 24<br>weft: 25 | warp: 25<br>weft: 23 | warp: 472<br>weft: 446 | 187 | Ether Grade<br>Great hydrolysis resistance<br>Soft, great resilience and flexibility<br>Suitable for high frequency welding<br>Good to bond with fabric and non-woven fabric<br>Processing for apparel |
| 19 | 80A | 1.06 | warp: 291<br>weft: 291 | warp: 76<br>weft: 73 | warp: 134<br>weft: 144 | warp: 536<br>weft: 518 | 80 | Non-yellowing<br>Good bonding to leather, fabric and PVC<br>Digital device case wrapping and other genuine leather wrapping<br>Hot melt film for sports shoes<br>Suitable for low temperature process |

Items 1-17 are ester based, items 18 and 19 are ether based

The invention claimed is:

1. A method of manufacturing a flexible and stretchable strain sensor, the method comprising:

printing an electrode layer onto a substrate with a first conductive ink;

printing a sensing layer onto the electrode layer with a second conductive ink; and encapsulating the electrode and sensing layers by applying a hot-melt layer, wherein ÷ the first conductive ink exhibits a sheet resistance less than that of the second conductive ink, wherein the electrode layer and sensing layer are in direct contact, wherein the electrode layer, the substrate, the first conductive ink, the second conductive ink and/or the hot-melt layer have elastomeric properties, and, wherein the sensor is configured such that an application of external force to or near the sensor generates microscopic cracks within the sensing layer increasing electrical resistance of the sensor, and the removal of the external force substantially eliminates the microscopic cracks within the sensing layer decreasing electrical resistance of the sensor.

2. The method of claim 1, further comprising applying heat to the hot-melt layer to adhere the sensor to a fabric.

3. The method of claim 2, wherein the sensor is integrated between two layers of fabric.

4. The method of claim 1, wherein the first conductive ink comprises silver (Ag).

5. The method of claim 1, wherein the sheet resistance of the first conductive ink at a thickness of 25 μm is less than 1 ohm.

6. The method of claim 1, wherein the second conductive ink comprises carbon (C).

7. The method of claim 1, wherein the sheet resistance of the second conductive ink at a thickness of 25 μm is at least 10 ohms.

8. The method of claim 1, wherein the electrode layer comprises a first electrode and a second electrode.

9. The method of claim 8, wherein: the electrode layer is generally elongate, the first and the second electrode each comprise a head portion and a tail portion, and the tail portions of the first and the second electrode are substantially parallel.

10. The method of claim 9, wherein the tail portions are each configured in repeating wave patterns.

11. The method of claim 9, wherein the head portions of the first and the second electrodes comprise a plurality of digitations configured to interdigitate the heads of the first and the second electrodes.

12. The method of claim 9, wherein the sensing layer is confined to head portions of the first and the second electrodes.

13. A method of manufacturing a flexible and stretchable strain sensor, the method comprising:

printing a generally elongate electrode layer with an Ag-containing conductive ink onto a substrate, the substrate comprising a thermoplastic ester-based polyurethane film of a thickness ranging from about 50 μm to about 1000 μm and a melting point of above about 100° C., the electrode layer comprising a first and second electrode, each electrode having a head and tail portion, the head portions of the first and second electrode being interdigitated;

printing a sensing layer directly onto the interdigitated portion of the electrode layer, the sensing layer comprising a C-containing conductive ink; and encapsulating the electrode and sensing layers by applying a hot-melt layer comprising an ester-based polyurethane film of thickness ranging from about 10 μm to about 100 μm and a melting point below about 100° C.;

wherein the sensor is configured such that:

the application of external force to or near the sensor generates microscopic cracks within the sensing layer, thereby increasing electrical resistance of the sensor, and the removal of the external force substantially eliminates the microscopic cracks within the sensing layer, thereby decreasing electrical resistance of the sensor.

14. A flexible and stretchable strain sensor comprising:

an electrode layer printed on a substrate, the electrode layer comprising a first conductive ink;

a sensing layer printed on a portion of the electrode layer, the sensing layer comprising a second conductive ink; and an encapsulation layer which encapsulates the electrode layer and the sensing layer, wherein the first conductive ink exhibits a sheet resistance less than that of the second conductive ink, wherein the sensing layer is in direct contact with the electrode layer, wherein the electrode layer, the substrate, first conductive ink, the second conductive ink and/or the encapsulation layer have elastomeric properties, and wherein the sensor is configured such that an application of external force to or near the sensor generates microscopic cracks within the sensing layer increasing electrical resistance of the sensor, and the removal of the external force substantially eliminates the microscopic cracks within the sensing layer decreasing electrical resistance of the sensor.

15. The sensor according to claim 14, wherein the first conductive ink comprises silver (Ag).

16. The sensor according to claim 14, wherein the sheet resistance of the first conductive ink at a thickness of 25 μm is less than 1 ohm.

17. The sensor according to claim 14, wherein the second conductive ink comprises carbon (C).

18. The sensor according to claim 14, wherein the sheet resistance of the second conductive ink at a thickness of 25 μm is at least 10 ohms.

19. The sensor according to claim 14, wherein:

the electrode layer is generally elongate, the first conductive ink forming a first electrode and a second electrode, and the first electrode and the second electrode each comprises a head portion and a tail portion, wherein the tail portions of the first and the second electrodes are substantially parallel.

20. The sensor according to claim 19, wherein the tail portions are each configured in a repeating wave pattern.

21. The sensor according to claim 19, wherein the head portions of the first and the second electrodes comprise a plurality of digitations configured to interdigitate the heads portions of the first and the second electrodes.

22. The sensor of claim 21, further comprising: a head region defined by the interdigitated portions of the first and the second electrodes, and a tail region defined by the tail portions of the first and the second electrode, wherein a ratio of a width of the head region to a width of the tail region is from about 1:1 to about 1:3.

23. The sensor of claim 19, wherein the sensing layer is confined to the head portions of the interdigitated portion of the first and the second electrodes.

24. The sensor of claim 14, wherein the substrate comprises a paper liner.

25. The sensor of claim 14, wherein the encapsulation layer is configured to adhere the sensor to a fabric material.

* * * * *